(12) United States Patent
Mihashi et al.

(10) Patent No.: US 7,441,900 B2
(45) Date of Patent: Oct. 28, 2008

(54) CONTRAST CHART DEVICE, CONTRAST SENSITIVITY MEASURING DEVICE AND CONTRAST SENSITIVITY MEASURING METHOD

(75) Inventors: Toshifumi Mihashi, Tokyo (JP); Yoko Hirohara, Tokyo (JP)

(73) Assignee: Topcon Corporation, Tokyo (JP)

( * ) Notice: Subject to any disclaimer, the term of this patent is extended or adjusted under 35 U.S.C. 154(b) by 746 days.

(21) Appl. No.: 10/467,159

(22) PCT Filed: Feb. 7, 2002

(86) PCT No.: PCT/JP02/01043

§ 371 (c)(1),
(2), (4) Date: Jan. 5, 2004

(87) PCT Pub. No.: WO02/062208

PCT Pub. Date: Aug. 15, 2002

(65) Prior Publication Data

US 2004/0095556 A1 May 20, 2004

(30) Foreign Application Priority Data

Feb. 8, 2001 (JP) .............................. 2001-032895
Dec. 28, 2001 (JP) .............................. 2001-401812

(51) Int. Cl.
*A61B 3/02* (2006.01)
(52) U.S. Cl. ..................... 351/239; 351/243; 351/211
(58) Field of Classification Search .................. 351/239
See application file for complete search history.

(56) References Cited

U.S. PATENT DOCUMENTS

| 4,155,632 | A |   | 5/1979 | Wolbarsht |
| 4,493,539 | A |   | 1/1985 | Cannon, Jr. |
| 4,511,228 | A |   | 4/1985 | Von Gierke et al. |
| 5,141,305 | A |   | 8/1992 | Young |
| 5,684,562 | A | * | 11/1997 | Fujieda ........................ 351/212 |
| 5,907,388 | A | * | 5/1999 | Fujieda ........................ 351/211 |
| 5,980,042 | A |   | 11/1999 | Hosoi |
| 6,000,799 | A | * | 12/1999 | Van de Velde ............... 351/205 |

FOREIGN PATENT DOCUMENTS

| DE | 197 38 810 A1 | 3/1999 |
| EP | 0 756 246 A1 | 1/1997 |
| EP | 0 838 193 A1 | 4/1998 |
| JP | 52-115595 A | 9/1977 |
| JP | 01-270846 A | 10/1989 |
| JP | 02-268730 A | 11/1990 |
| JP | 06-165754 A | 6/1994 |
| JP | 2848917 B2 | 11/1998 |
| JP | 11-137521 A | 5/1999 |
| JP | 11-212526 A | 8/1999 |
| JP | 2000-262475 A | 9/2000 |

* cited by examiner

*Primary Examiner*—Jessica T Stultz
(74) *Attorney, Agent, or Firm*—Foley & Lardner LLP

(57) ABSTRACT

A contrast chart device of the present invention comprises a contrast target presenting part for presenting a contrast target for a contrast sensitivity test at prescribed timing; a pupil data measuring part for producing an image of an anterior ocular segment of a subject and measuring the diameter or area of a pupil region in the anterior ocular segment; and a measurement timing forming part for forming timing at which the pupil data measuring part performs measurement.

35 Claims, 16 Drawing Sheets

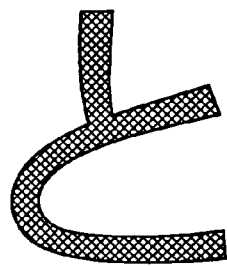
FIG. 2(A)  100%  ☐ Pedestal target : 100%
▨ Test target : 0%
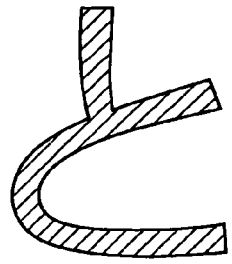
FIG. 2(B)  60%  ☐ Pedestal target : 100%
▨ Test target : 40%
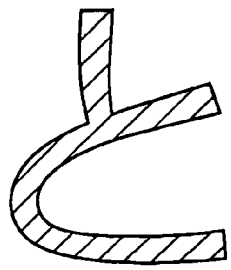
FIG. 2(C)  20%  ☐ Pedestal target : 100%
▨ Test target : 80%

FIG. 5(A)
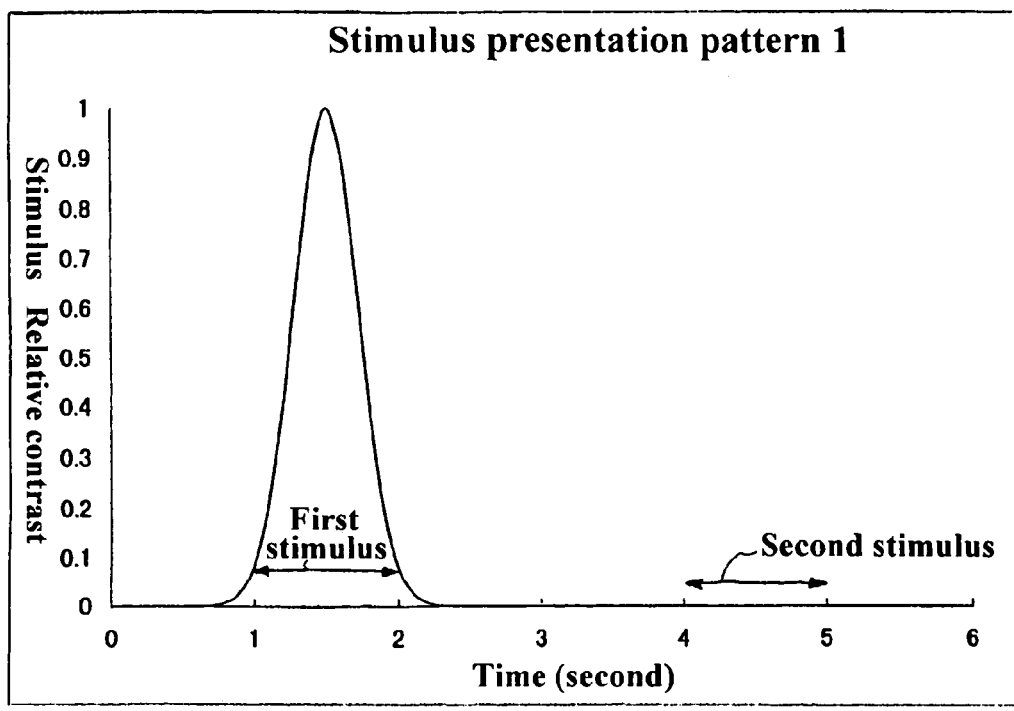
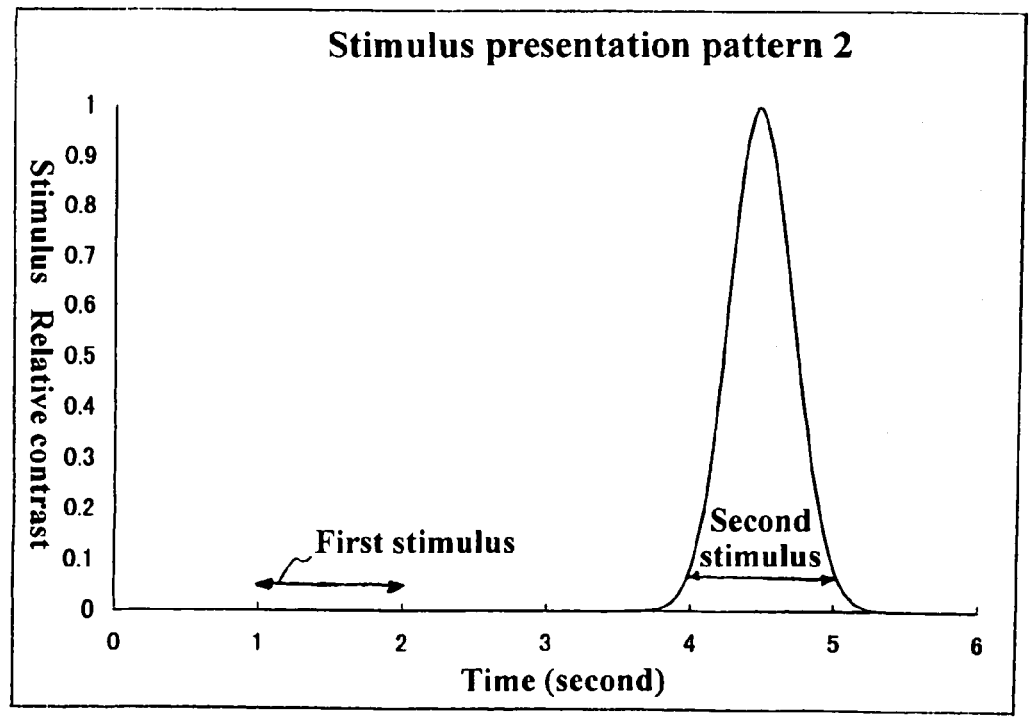
FIG. 5(B)

FIG. 10(A)
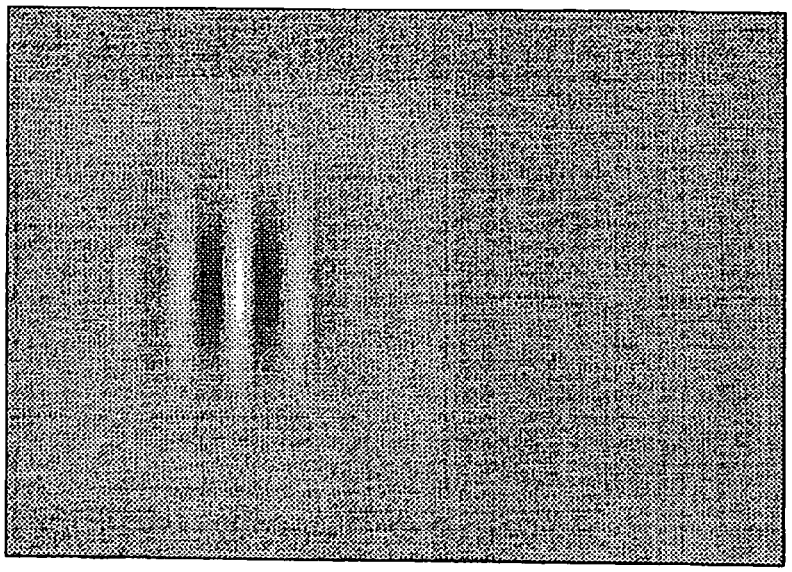
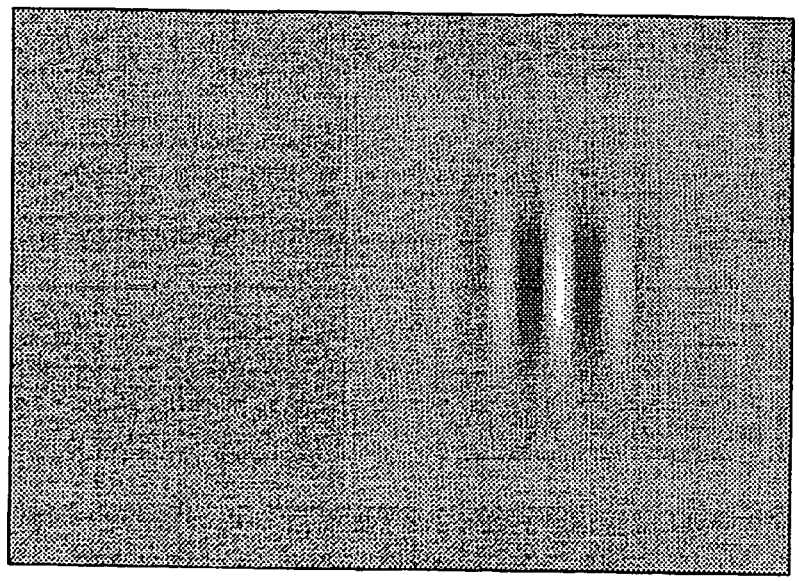
FIG. 10(B)

FIG. 11(A) 3cpd
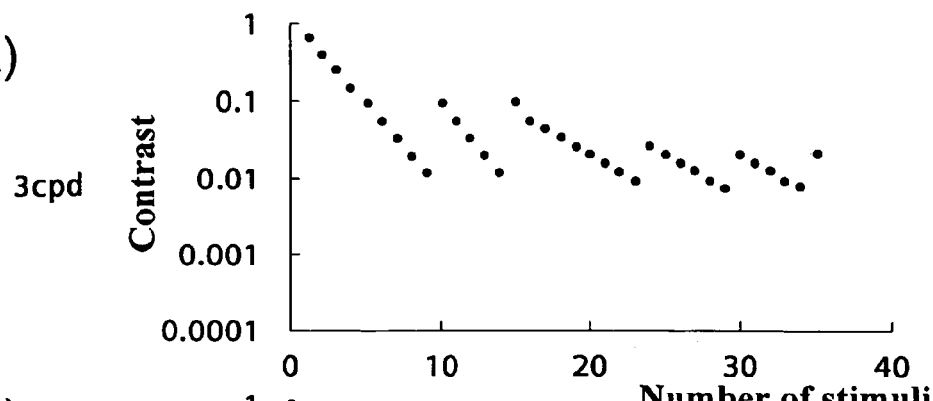
FIG. 11(B) 6cpd
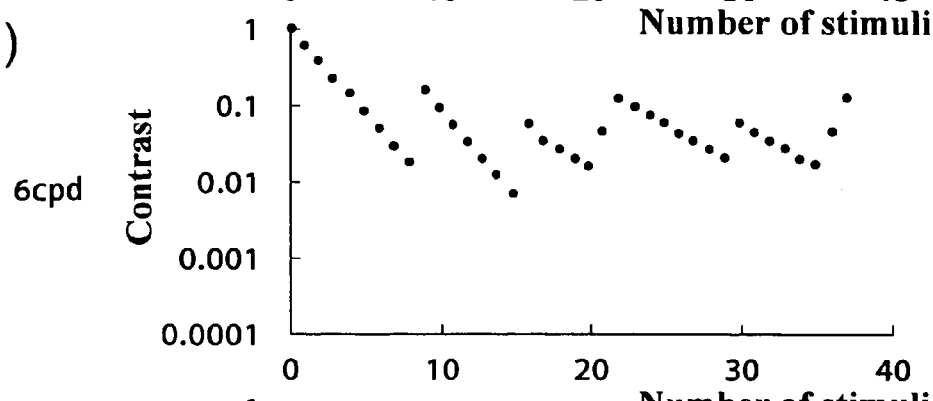
FIG. 11(C) 12cpd
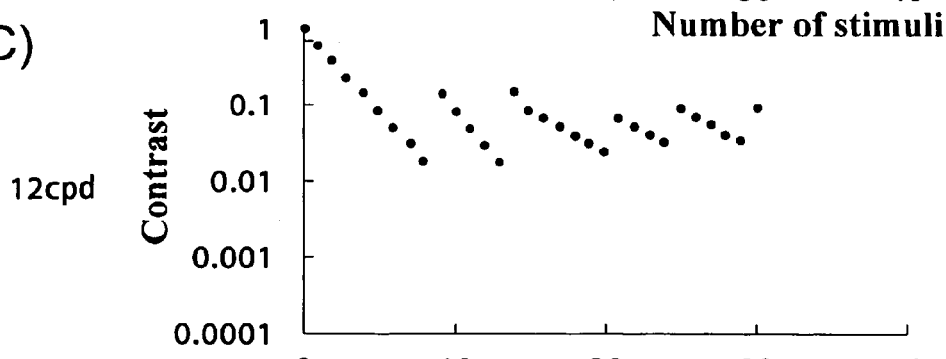
FIG. 11(D) 18cpd
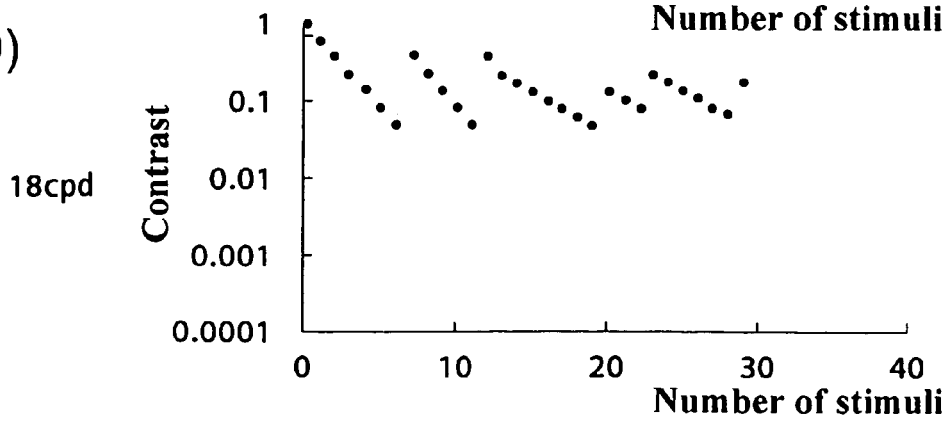

CONTRAST CHART DEVICE, CONTRAST SENSITIVITY MEASURING DEVICE AND CONTRAST SENSITIVITY MEASURING METHOD

TECHNICAL FIELD

The present invention relates to a contrast sensitivity measuring device suitable for use in a visual acuity test using a contrast chart. More specifically, the present invention relates to a contrast chart device, a contrast sensitivity measuring device and a contrast sensitivity measuring method suitable for precisely determining the aberrations of an eye of a subject at the time of a laser optical surgery or improvement of visual acuity with glasses or contact lenses.

BACKGROUND ARTS

In recent years, optical surgeries by which the shapes of corneas are altered with laser are attempted. At the time of such a surgery, it is important to precisely measure the aberrations of the eye. Before and after a corneal surgery or a cataract surgery, visual function tests, including measurement of visual acuity, a low-contrast visual acuity test (which is also referred to as "contrast visual acuity test") and a contrast sensitivity test, are performed.

Here, a general visual acuity test using a standard visual acuity chart measures the visual acuity to a minute object with a high contrast ratio. Then, in a cataract patient, for example, turbidity of a crystalline lens causes scatter of light, which lowers the contrast of an image on the fundus but does not affect deviation of the optical focus position of the image. As a result, the cataract patient as a subject may be able to read the image as a letter although the image on the fundus is blur. Also, in the case where a spherical aberration is caused by optical distortion of a cornea and a crystalline lens, the subject may be able to read the image as a letter although the image on the fundus is blur.

Contrast sensitivity which represents the ability to detect a specific object with a minimum contrast is an important index to express the visual ability of a subject in daily and social life. Thus, in measurement of contrast sensitivity, a sine wave grid pattern is used to examine a single modulation transfer function. A sine wave grid pattern is a grid pattern in which the density varies in a sine wave pattern. In a contrast sensitivity test, the minimum contrast necessary to recognize a grid pattern is measured at various finenesses (spatial frequencies).

However, since a contrast sensitivity test is performed in such a manner that a subject (patient) reads a visual acuity chart under examiner's direction, there are the following problems.
(1) As the test is performed using a single visual acuity chart, the subject remembers the visual acuity chart when trials are repeated. For example, when the left eye is examined after the right eye and when the visual acuity of the right eye is better than that of the left eye, the subject can respond correctly with memory even if it cannot see the chart with the left eye. Thus, it is difficult to measure the contrast sensitivity of a subject precisely.
(2) It takes about 10 minutes to measure contrast sensitivity and a clinical technologist or ophthalmologist must concentrate on the test during that time. Thus, the practice time or the examination time is unavoidably long.
(3) The diameter or area of the pupil region of a subject is preferably constant during measurement of contrast sensitivity. However, as the eye gets tired, the diameter or area of the pupil region of the subject varies and becomes different from the theoretical diameter or area of the pupil region of the subject. Thus, it is difficult to measure the contrast sensitivity of a subject precisely.

DISCLOSURE OF THE INVENTION

A first object of the present invention is to provide a contrast chart device which can obtain the aberrations of an eye to be examined with ease by measuring the contrast sensitivity and the pupil diameter thereof simultaneously.

A second object of the present invention is to provide a contrast sensitivity measuring device and a contrast sensitivity measuring method which can measure the contrast sensitivity of a subject precisely within a short period of time.

The contrast chart device and the contrast sensitivity measuring device herein are substantially the same. The contrast chart device is a name to emphasize the function of presenting a chart for use in measurement of contrast sensitivity and the contrast sensitivity measuring device is a name to emphasize the function of measuring contrast sensitivity.

The contrast chart device of the present invention comprises, as shown in FIG. 1, a contrast target presenting part 100 for presenting a contrast target for a contrast sensitivity test at prescribed timing; a pupil data measuring part 200 for producing an image of an anterior ocular segment 401 of a subject and measuring the diameter or area of a pupil region in the anterior ocular segment 401; and a measurement timing forming part 300 for forming timing at which the pupil data measuring part 200 performs measurement based on the prescribed timing. As the contrast target, a combination of a target for a general visual acuity test such as a Landolt ring target or a Snellen letter target and a pedestal target, or a target suitable for measurement of modulation transfer function (MTF) such a Gabor stimulus is used.

In a device constituted as above, the contrast target presenting part 100 present a contrast target to an eye 400 to be examined at a prescribed timing, and the subject responds whether it can see the presented contrast target. Thereby, the contrast sensitivity of the subject can be measured. The measurement timing forming part 300 forms a timing signal indicating the timing at which the pupil data measuring part 200 measures the pupil diameter of the subject based on the timing at which the contrast target presenting part 100 presents a contrast target to the eye 400 to be examined. Thus, the contrast sensitivity and the pupil diameter of the subject can be simultaneously measured.

Preferably, the contrast target presenting part 100 has a first illuminating optical system 110 for mainly forming targets and a second illuminating optical system 130 for mainly forming backgrounds, and is so constituted that luminous fluxes from the first illuminating optical system 110 and the second illuminating optical system 130 are combined, passed through a first mirror 152 for folding a light path, reflected by a second mirror 153, and reflected again by the first mirror 152 to an eye 400 to be examined. Thereby, the contrast produced by a target and a background can be easily adjusted.

The first illuminating optical system 110 is preferably so constituted that targets of various sizes can be selectively inserted into a light path therein. Thereby, the contrast sensitivity of a subject can be measured quickly. Also, the second illuminating optical system is preferably configured to be able to produce a luminous flux with uniform light distribution in different brightnesses. Thereby, a combination of a target and a background to produce a desired contrast can be easily obtained.

Preferably, the pupil data measuring part 200 is configured to produce the image of an anterior ocular segment 401 of the subject and measure the diameter or area of a pupil region in the anterior ocular segment 401 through the first mirror 152. Thereby, the pupil data measuring part 200 and the contrast target presenting part 100 can share an optical system and the structure can be simplified. The pupil data measuring part 200 may be configured to measure the pupil diameter of the subject when the contrast timing forming part 300 sends a present timing signal to the contrast target presenting part 100 or the subject makes a response.

When the contrast chart divice is configured to be able to output to a divice for measuring the wavefront aberrations of the eye at least the measured pupil diameter of the subject and a contrast target presented when the pupil diameter is measured, the aberrations of the eye to be examined can be measured taking the pupil diameter therof into consideration. Thus, in an optical surgery in which the shape of a cornea or the like is changed with a laser beam, the spot on the cornea where a laser beam should be applied can be easily determined.

The contrast sensitivity measuring device of the present invention comprises, as shown in FIG. 8, a contrast target presenting part 100 for presenting first and second contrast targets side by side; a pupil data measuring part 200 for producing an image of an anterior ocular segment of a subject and measuring the diameter or area of a pupil region in the anterior ocular segment; and a measurement timing forming part 300 for forming timing at which the pupil data measuring part 200 performs measurement based on the timing at which the contrast target presenting part 100 presents the first and second contrast targets.

In a device constituted as above, the contrast target presenting part 100 presents the first and second contrast targets side by side. Thus, a contrast target including information useful for the measurement can be freely switched between the first and second contrast target positions. This makes the memory of the subject on the positions of the contrast targets in a previous trial useless and makes it possible to measure the contrast sensitivity precisely based on the positions of the contrast targets visually recognized by the subject. The pupil data measuring part 200 measures either or both of the diameter and area of the pupil region of the subject, so that the contrast target presenting part 100 can make the diameter or area of the pupil region of the subject constant. This improves the degree of freedom for the measurement. Also, since the measurement is automatically performed by the measuring timing forming part 300, the operation of the clinical technologist or ophthalmologist is facilitated.

Preferably, one of the first and second contrast targets is a target with a contrast of 0 and the other is a target with a contrast for measuring contrast sensitivity. The first and second contrast targets may have a brightness which may be different from or the same as that of the background. Preferably, a contrast target useful for measurement of contrast sensitivity is one of the first and second contrast targets.

The contrast sensitivity measuring device of the present invention comprises, as shown in FIG. 8, a contrast target presenting part 100 for presenting a contrast target in at least one of two positions at random; a pupil data measuring part 200 for producing an image of an anterior ocular segment of a subject and measuring the diameter or area of a pupil region in the anterior ocular segment; and a measurement timing forming part 300 for forming timing at which the pupil data measuring part 200 performs measurement based on the timing at which the contrast target presenting part 100 presents the contrast target.

Preferably, the contrast target presenting part 100 has target brightness adjusting means 125 for adjusting the brightness of the contrast target or contrast targets; and target brightness control means 120 which receives the diameter or area of the pupil region of the subject measured by the pupil data measuring part 200 and sends a brightness control signal to the target brightness adjusting means 125 so that the diameter or area of the pupil region will be a prescribed value. In the device constituted as above, the diameter or area of the pupil region of a subject can be constant by adjusting the brightness of the contrast target or contrast targets. This makes it possible to measure the contrast sensitivity precisely.

Preferably, the contrast target presenting part 100 has background illumination adjusting means 145 for adjusting a background illumination of the contrast target or contrast targets; and background illumination control means 140 which receives the diameter or area of the pupil region of the subject measured by the pupil data measuring part 200 and sends a background illumination control signal to the background illumination adjusting means 145 so that the diameter or area of the pupil region will be a prescribed value. In the device constituted as above, the diameter or area of the pupil region of a subject can be constant by adjusting the background illumination of the contrast target or contrast targets. This makes it possible to measure the contrast sensitivity precisely.

Preferably, the contrast target presenting part 100 has, as shown in FIG. 8, brightness/illumination adjusting means (120, 140) for adjusting at least one of the brightness of the contrast target or contrast targets and illuminance of a background illumination of the contrast target or contrast targets in order to maintain the retinal illuminance of the subject at a generally prescribed value. By maintaining the retinal illuminance of a subject at a generally prescribed value, the conditions under which the contrast sensitivity is measured can be kept constant in an environment in which the brightness is significantly different between the daytime and nighttime periods. This makes it possible to measure the contrast sensitivity precisely.

Preferably the pupil data measuring part 200 is configured to produce an image of the anterior ocular segment 401 of the subject and measure the diameter or area of the pupil region of the subject before and when the measurement of contrast sensitivity is performed. Thereby, the contrast target presenting part 100 can easily make the diameter or area of the pupil region of a subject constant. For example, even when too much or little adjustment was made, the amount to be adjusted next can be easily determined.

Preferably, the pupil data measuring part 200 is configured to measure the diameter or area of the pupil region of the subject when the contrast target or contrast targets is or are presented or the subject makes a response. For the timing when the subject makes a response, the clinical technologist inputs the timing when the subject makes a response using a subject response device 310 such as a mouse or with voice.

Preferably, the contrast sensitivity measuring device further comprises, as shown in FIG. 8, an anterior ocular segment illuminating part 500 for illuminating an anterior ocular segment; and anterior ocular segment illumination control means 510 which receives the diameter or area of the pupil region of the subject measured by the pupil data measuring part 200 and sends an illumination control signal to the anterior ocular segment illuminating part 500 so that the diameter or area of the pupil region will be a prescribed value. In the device constituted as above, the diameter or area of the pupil region of a subject can be constant by adjusting the anterior ocular segment illuminating part 500. This makes it possible to measure the contrast sensitivity precisely.

Preferably, the contrast sensitivity measuring device further comprises, as shown in FIG. 14, a luminance measuring part 160 for measuring the luminance of the contrast target or contrast targets presented by the contrast target presenting part 100; and a luminance correcting part 162 for correcting the luminance of the contrast target or contrast targets based on the luminance measured by the luminance measuring part 160. For example, the luminance correcting part 162 is configured to send a correction signal to the target brightness adjusting means 125 of the contrast target presenting part 100 to correct the luminance of the contrast target or contrast targets.

Preferably, the contrast sensitivity measuring device further comprises, as shown in FIG. 14, retinal illuminance calculating means 550 for calculating the retinal illuminance of the eye to be examined from the diameter or area of the pupil region of the eye to be examined and the brightness of the contrast target or contrast targets; and retinal illuminance adjusting means 560 for outputting an adjusting signal so that the retinal illuminance of the eye to be examined will be generally constant, and configured to measure the contrast sensitivity of the eye to be examined with the retinal illuminance of the eye to be examined maintained generally constant. For example, the retinal illuminance adjusting means 560 is configured to output a signal for adjusting the brightness of the contrast target or contrast targets to the target brightness adjusting means 125, output a signal for adjusting the brightness of the background illumination of the contrast target or contrast targets to the background illumination adjusting means 145, or output a signal for adjusting the brightness of the anterior ocular segment illuminating part 500 to the anterior ocular segment illumination control 510.

Preferably, the contrast sensitivity measuring device further comprises, as shown in FIG. 14, pupil diameter contrast sensitivity converting means 570 which reads the diameter or area of the pupil region of the subject at the time of measurement of contrast sensitivity from the pupil data measuring part 200 and converts a measured contrast sensitivity into a contrast sensitivity which would be obtained when the pupil diameter is a reference value.

The contrast sensitivity measuring method of the present invention comprises steps of presenting a contrast target for a contrast sensitivity test at a prescribed timing; generating a measurement timing signal indicating the timing at which the diameter or area of a pupil region of a subject is measured based on the timing at which the contrast target is presented; and producing an image of an anterior ocular segment of the subject at the timing indicated by the measurement timing signal and measuring the diameter or area of the pupil region of the subject.

Preferably, the contrast target for a contrast sensitivity test comprises two contrast targets presented side by side and at least one of the two contrast targets is presented as a contrast target useful for a contrast sensitivity test. This makes it possible to measure the contrast sensitivity precisely. Preferably, the contrast target for a contrast sensitivity test is presented in at least one of two positions at random so that the subject cannot predict in which position the contrast target will be presented. This makes it possible to measure the contrast sensitivity precisely.

The application is based on the Patent Application No. 2001-032895 filed on Feb. 8, 2001 and the Patent Application No. 2001-401812 filed on Dec. 28, 2001 in Japan, the content of which is incorporated herein, as part thereof.

Also, the invention can be fully understood, referring to the following description in details. Further extensive applications of the invention will be apparent from the following description in details. However, it should be noted that the detailed description and specific examples are preferred embodiments of the invention, only for the purpose of the description thereof. It is apparent for the person ordinarily skilled in the art to modify and change in a variety of manners within the scope and spirits of the invention.

The Applicant does not intend to dedicate any disclosed embodiments to the public, and to the extent any disclosed modifications or alternations may not literally fall within the scope of the claims, they are considered to be part of the invention under the doctrine of the equivalents.

BRIEF DESCRIPTION OF THE DRAWINGS

FIGS. 2(A)-2(C) are explanatory views of contrast using test targets for a general visual acuity test;

FIGS. 5(A) and 5(B) are explanatory views of stimulus presenting patterns for use in the up-down method shown in FIG. 4;

FIGS. 10(A) and 10(B) are explanatory views illustrating examples of the contrast sensitivity target presented in the up-down method;

FIGS. 11(A)-11(D) are views illustrating an example of the history of responses of a subject about contrast sensitivity targets with various spatial frequencies;

BEST MODE FOR CARRYING OUT THE INVENTION

First Embodiment

Figure 1:
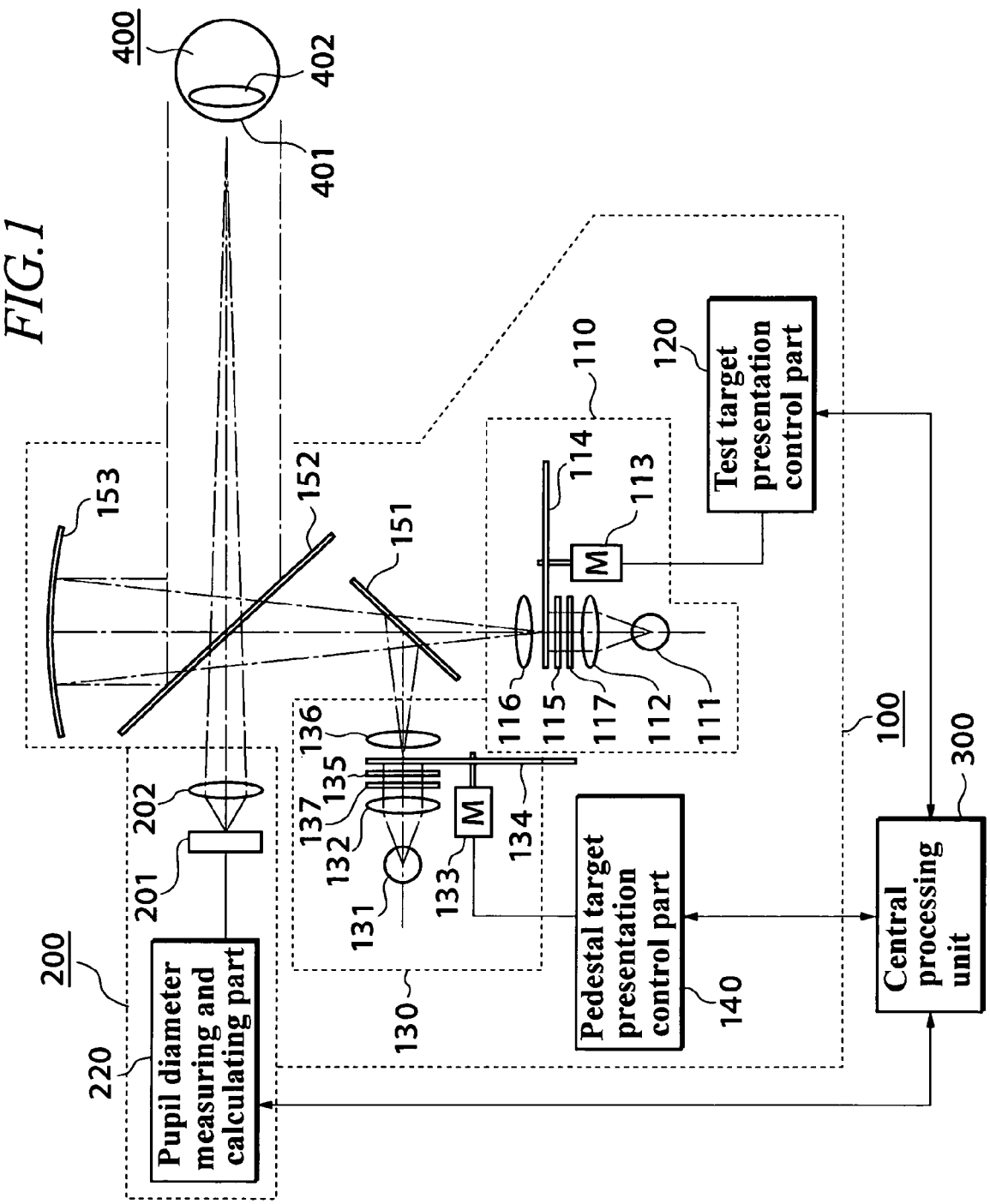
FIG. 1 is a structural view illustrating a first embodiment of the present invention.

Description will be hereinafter made of the embodiments of the present invention with reference to the drawings. The same or corresponding components are denoted in all the drawings by the same or similar numerals and the overlapped description will be omitted. FIG. 1 is a structural view illustrating a first embodiment of the present invention, in which an optical system and a control system are shown. As shown in FIG. 1, a contrast target presenting part 100 has a first illuminating optical system 110, a test target presentation control part 120, a second illuminating optical system 130 and a pedestal target presentation control part 140.

The first illuminating optical system 110 is for mainly forming test targets and has a light source 111, a condenser lens 112, a target exchanging rotary motor 113, a target plate 114, an ND filter 115, magnification correction lenses 116 and a diffusion plate 117. The condenser lens 112 collimates light emitted from the light source 111. On the target plate 114, test targets for a general visual acuity test such as Landolt rings and Snellen's letters, or test targets for a contrast sensitivity test suitable for measurement of modulation transfer function such as Gabor stimuli are printed as contrast targets in prescribed sizes. As the targets for a general visual acuity test, various types of letters and marks are drawn in widths which form visual angles corresponding to the visual acuities of 0.1, . . . , 2.0 (a visual angle of 1 arc minute corresponds to a visual acuity of 1.0). As contrast sensitivity targets, stripe patterns with special frequencies of 1.5, 3, 6, 12, and 18 [cycles/deg] at a visual distance of 3 m are drawn.

The ND (neutral density) filter 115 is a filter only for changing the quantity of light to, for example, 60% or 40% and does not bring about polarization and so on. The magnification correction lenses 116 have a focal distant of infinity (0 diopter), 5 m (0.2 diopter) and so on. An adjustment is made by exchanging the magnification correction lenses 116 when the test targets are presented to a subject. The diffusion plate 117 diffuses light emitted from the condenser lens 112 to make light quantity distribution uniform.

The second illuminating optical system 130 is for mainly forming backgrounds such as pedestal targets, and has a light source 131, a condenser lens 132, a target exchanging rotary motor 133, a target plate 134, an ND filter 135, magnification correction lenses 136, and a diffusion plate 137. The second illuminating optical system 130 is constituted of generally the same types of optical members as those of the first illuminating optical system 110, but different therefrom in that the targets printed on the target plate 134 are backgrounds. Since the contrast targets for use in a general visual acuity test on the target plate 114 have a contrast of 100%, the backgrounds with contrasts of 0%, 10%, 20%, . . . , 90% and so on are prepared on the target plate 134. As the contrast sensitivity targets, test targets, each having a prescribed spatial frequency and a prescribed contrast, are printed. Thus, on the target plate 134 are printed backgrounds to adjust the brightness of all the test targets to be almost the same.

A test target sent from the first illuminating optical system 110 and a pedestal target sent from the second illuminating optical system 130 are superimposed in a light path by a mirror 151, passed through a spectral mirror 152 as a first mirror, reflected by a concave mirror 153 as a second mirror, reflected again by the spectral mirror 152 and reaches an anterior ocular segment 401 of a subject. The mirror 151 may be a half mirror. The transmissivity and reflectivity of the mirror 151 may be determined depending upon the light quantities of the light sources 111 and 131. By properly determining the transmissivity and reflectivity of the mirror 151, energy efficiency can be improved as compared with the case where light is constantly attenuated by the ND filters 115 and 135. As anatomically known, an eye 400 to be examined of a subject has the anterior ocular segment 401 including a cornea and a crystalline lens 402.

The test target presentation control part 120 drives the target exchanging rotary motor 113 to move the target plate 114 to a suitable position so that an appropriate test target can be presented to a subject. The pedestal target presentation control part 140 drives the target exchanging rotary motor 133 to move the target plate 134 to a suitable position so that a pedestal target having a contrast or brightness corresponding to that of the test target can be presented to a subject.

A pupil data measuring part 200 has a photoreceptor 201, a light detection camera lens system 202, and a pupil diameter measuring and calculating part 220. Since the optical systems regarding the targets use light of visible wavelengths, the pupil data measuring part 200 may use near infrared light or visible light of a wavelength which is different from that of the test targets. For the photoreceptor 201, an element which can receive a planar image such as a charged-coupled device (CCD) is used. The magnification of the light detection camera lens system 202 can be adjusted so that an image of a pupil is thrown on the photoreceptor 201 at an optimum magnification. The image of the anterior ocular segment 401 of a subject received by the photoreceptor 201 may include an image of a pupil or pupils. The pupil diameter measuring and calculating part 220 processes and recognizes the image of the anterior ocular segment 401 received by the photoreceptor 201 and outputs the diameter of the pupil on real time. The pupil diameter measuring part 200 may measure and output the area of the pupil instead of the pupil diameter. When the shape of the pupil is a perfect circle, the pupil diameter and pupil area include substantially the same information.

The central processing unit 300 as a measurement timing forming part generates a timing signal indicating the timing at which the pupil data measuring part 200 measures the pupil diameter of a subject based on the timing at which the contrast target presenting part 100 presents a contrast target to the anterior ocular segment 401 of the subject or the timing at which the subject makes a response. The central processing unit 300 also has a function of combining and processing information on the contrast presented by the contrast target presenting part 100, information on the visual acuity of a subject and information on the pupil diameter of the subject obtained by the pupil data measuring part 200.

FIG. 2 is an explanatory view of contrast using test targets for a general visual acuity test, in which (A) shows a contrast of 100%, (B) shows a contrast of 60%, and (C) shows a contrast of 20%. A simple and typical pedestal target is a target with a transmissivity of 100% or no interpositions and sent from the second illuminating optical system 130. As the test targets, letters, such as "と", with transmissivities of 0%, 40%, 80% and so on are printed on the target plate 114. Contrast is given as the difference between the transmissivities of a pedestal target and a test target. The test targets are printed on a chart for measuring visual acuity. Typical examples of the test targets are Landolt rings or letters drawn on a parallel flat glass plate by chrome plating. The Landolt rings or letters (foregrounds) have transmissivity of 100% and the background has a transmissivity of 0%, or the Landolt rings or letters have transmissivity of 0% and the background has a transmissivity of 100%. A white noise or a filtered noise stimulus with a limited bandwidth may be used as the pedestal target instead of a pedestal target with a transmissivity of 100%.

Description will be made of the process of measurement of contrast sensitivity using a device constituted as above. The operator inputs contrasts of test targets for a general visual acuity test to be presented to the anterior ocular segment 401 of a subject into the central processing unit 300. The central processing unit 300 drives the target exchanging rotary motors 113 and 133 to position the targets plates 114 and 134 so that the input contrasts can be produced. Then, the first and second illuminating optical systems 110 and 130 present targets with various contrasts according to the input by the operator to the anterior ocular segment 401 of the subject. The subject responds whether it can see or cannot see the targets. The operator can measure the contrast sensitivity of the subject by increasing or decreasing the contrast. At this time, the central processing unit 300 makes the pupil data measuring part 200 obtain information on the diameter of the pupil. Thus, the pupil diameter at the time of the measurement of contrast sensitivity can be obtained.

In the above first embodiment, an example in which the test targets are sent from the first illuminating optical system 110 and the pedestal targets are sent from the second illuminating optical system 130 has been described. However, the target plates 114 and 134 may be interchanged so that the pedestal targets are sent from the first illuminating optical system 110 and the test targets are sent from the second illuminating optical system 130. Also, in the above embodiment, the contrast produced by a pedestal target and a test target is varied using the target plate 114. However, the contrast may be varied by changing the light quantity of the light source 131 and/or the light source 111 or the transmissivity (density) of the ND filter 135 and/or the ND filter 115. Also, an example in which a single test target as shown in FIG. 2 is presented at a time has been described. However, a plurality of test targets based on a psychophysical experiment method such as a constant method or an up-down method may be presented at a time. When composite targets, such as a conventional JIS chart or ETDRS chart, are presented as the test targets, a JIS chart or ETDRS chart with a contrast of 10%, 100%, etc. can be realized with ease.

Figure 3A:
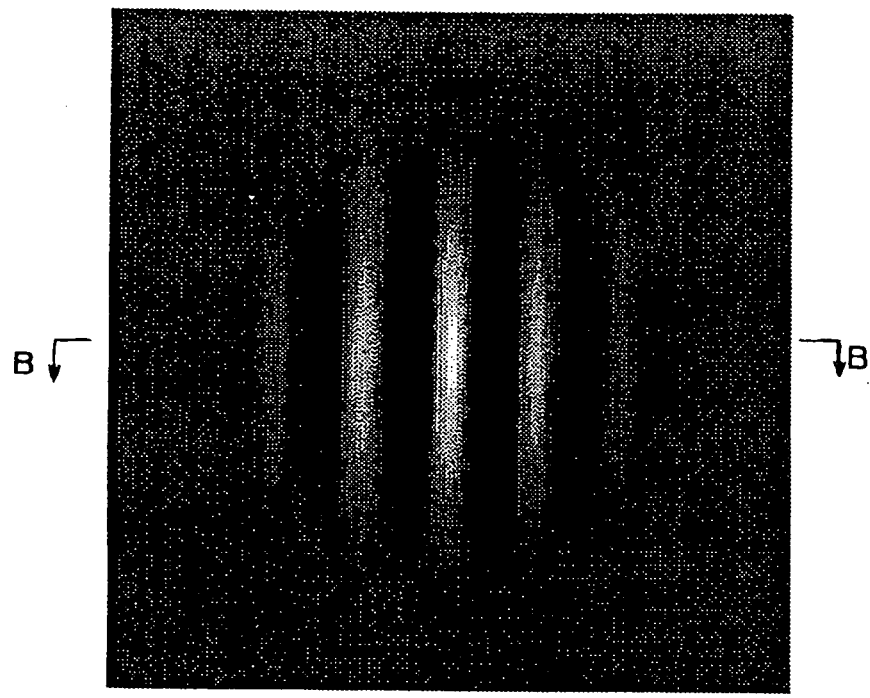
FIGS. 3(A) and 3(B) are explanatory views of contrast using a contrast sensitivity target.
Figure 3B:
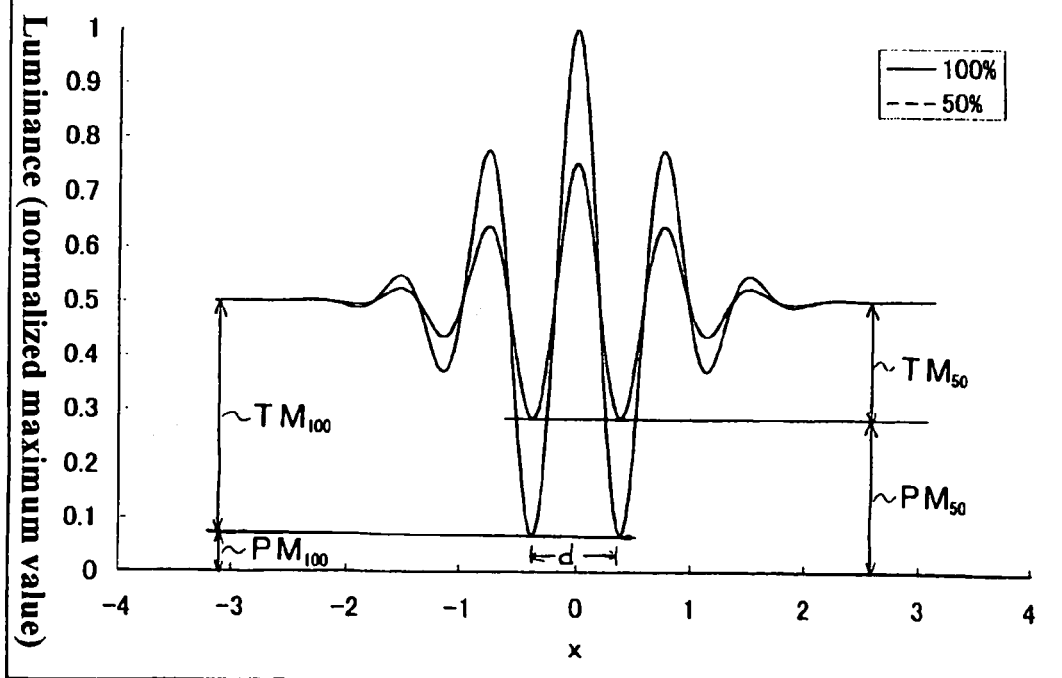

FIG. 3 is an explanatory view of contrast using a contrast sensitivity target, in which (A) is a plan view of a Gabor stimulus to be thrown on the anterior ocular segment of a subject, and (B) shows the luminance profile of the contrast chart in the direction of B-B in (A). The peak interval "d" of the luminance profile corresponds to the spatial frequency. When the contrast is 100%, since the luminance amplitude of a test target $TM_{100}$ using the Gabor stimulus is large, the luminance of a pedestal target $PM_{100}$ is about 0.08, which is the minimum luminance of the Gabor stimulus. When the contrast is 50%, since the luminance amplitude of the test target $TM_{50}$ using the Gabor stimulus is smaller than that of the test target $TM_{100}$, the luminance of a pedestal target $PM_{50}$ is about 0.28, which is the minimum luminance of the Gabor stimulus.

Namely, in a plan view of a Gabor stimulus. the luminance amplitude of a test target varies depending upon the contrast. Thus, a pedestal target having an appropriate transmissivity must be selected depending upon the luminance amplitude of the Gabor stimulus so that the contrast sensitivity targets can have the same brightness. Therefore, the central processing unit 300 drives the target exchanging rotary motors 113 and 133 to obtain a suitable combination of targets on the target plates 114 and 134. The central processing unit 300 may be able to adjust the light quantity of the light sources 111 and 131 or the trasnmissivity of the ND filter 115 and 135 to equalize the brightness of the contrast sensitivity targets.

Figure 4:
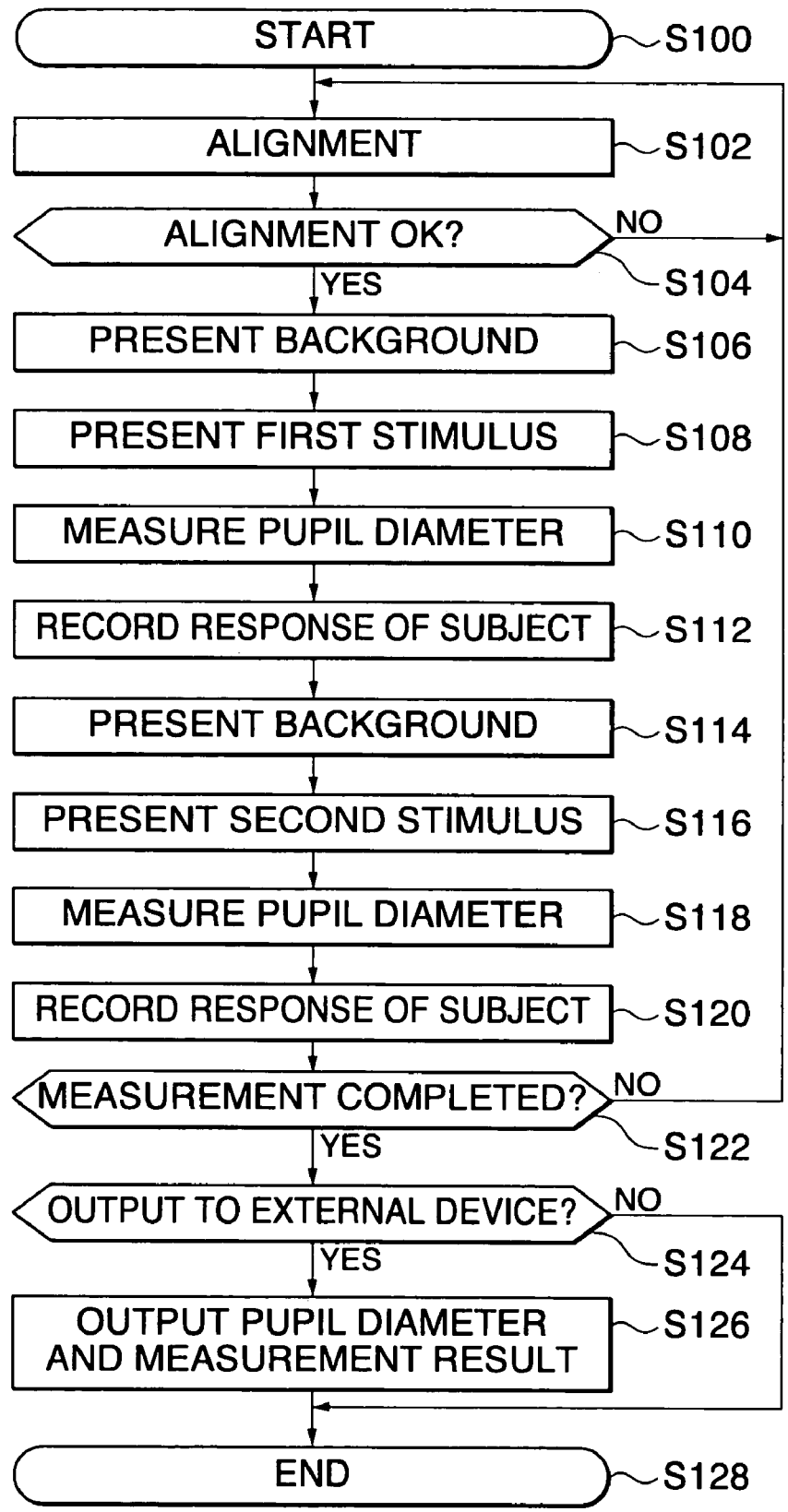
FIG. 4 is a flowchart for explaining the procedure for measuring contrast sensitivity by an up-down method using the contrast sensitivity target shown in FIG. 3.

FIG. 4 is a flowchart for explaining the procedure for measuring contrast sensitivity by an up-down method using the contrast sensitivity target shown in FIG. 3. The up-down method, which is one of psychological measurement methods, is a forced choice method in which two stimuli are presented in a trial and the subject answers which one has a Gabor stimulus. When the measurement of contrast sensitivity is started (S100), alignment is performed (S102), and the optical systems are adjusted so that an image of a Gabor stimulus is focused on the anterior ocular segment 401 of the subject (S104). When the alignment adjustment is completed, a background is presented to the subject (S106) and then a first stimulus of the Gabor stimulus is presented (S108). Then, the pupil diameter is measured (S110) and the response of the subject is recorded (S112). Then, the background is presented again to the subject (S114) and a second stimulus of the Gabor stimulus is presented (S116). Then, the pupil diameter is measured (S118) and the response of the subject is recorded (S120).

The central processing unit 300 judges whether the measurement has been completed (S122) The central processing unit 300 presents the first and second stimuli of the Gabor stimulus alternately to the subject until the measurement is completed. When the measurement is completed, the central processing unit 300 judges whether to output to an external device (S124). When necessary, the central processing unit 300 outputs the contrast sensitivity measured using Gabor stimuli and pupil diameter information to a relevant external device (S126). Thereby, the measurement of contrast sensitivity on the subject is completed (S128).

FIG. 5 is an explanatory view of stimulus presenting patters for use in the up-down method shown in FIG. 4, in which (A) shows a stimulus presentation pattern 1 and (B) shows a stimulus presentation pattern 2. In both stimulus presentation patterns 1 and 2, a beep is sounded to inform the subject of the start of presentation of stimuli at 00:00, and a first stimulus is presented for 1 second from 00:01 to 00:02 and a second stimulus is presented for 1 second from 00:04 to 00:05. From 00:00 to 00:01, from 00:02 to 00:04 and from 00:05 to 00:06, a background is presented to the subject. In the stimulus presentation pattern 1, a Gabor stimulus is presented as the first stimulus and not presented as the second stimulus. In the stimulus presentation pattern 2, a Gabor stimulus is presented as the second stimulus and not presented as the first stimulus. The contrast of the Gabor stimulus is varied in a Gaussian curve during about one second. During the one second, the relative stimulus contrast is varied from 0.1 to 1.0 to 0.1 smoothly.

Figure 6:
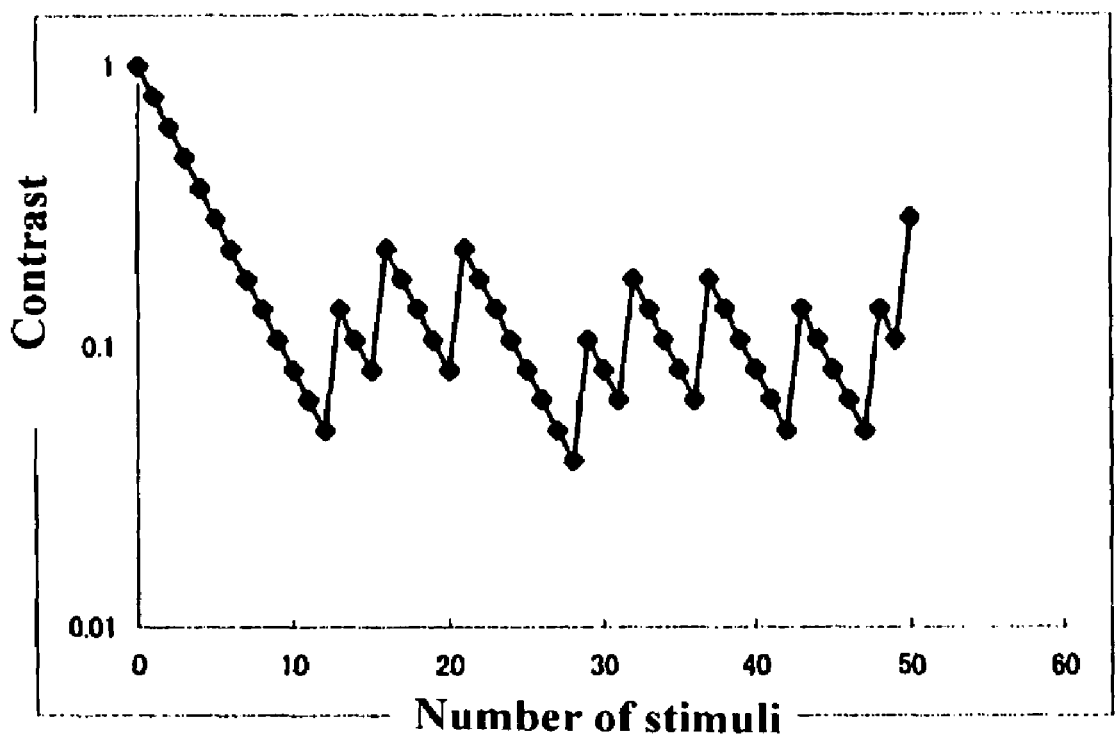
FIG. 6 is a graph showing an example of the change in contrast in the up-down method shown in FIG. 4.

FIG. 6 is a graph showing an example of the change in contrast in the up-down method shown in FIG. 4, in which the contrast is plotted on the horizontal axis and the number of stimuli on the vertical axis. The measurement is started from a contrast of 100% (shown as 1 in the graph), and every time the subject makes a correct response, the contrast of the stimulus is decreased by 0.1 in logarithm at a time. When the subject makes a wrong response, the contrast of the stimulus is increased by, for example, four steps. When the subject makes a wrong responds five times in each ups and downs, the measurement is completed. The contrast sensitivity of the subject is the average of the ten contrast sensitivities at which the subject made a wrong response, for example 0.06 ($=10^{-1.2}$).

When the results obtained in the contrast measurement according to the up-down method are classified into, for example, 5 contrast levels, the average $s_0$ and dispersion of the contrast threshold values can be obtained by probit analysis, which is one of statistical analysis methods. When the modulation transfer function MTF of the optical systems has been obtained with a wavefront sensor or the like, the modulation transfer function MTF of the optic nerve system can be calculated by the following equation;

$$M_{lat}(u) = k \cdot m_n \cdot M_{opt}(u)/m_t \tag{1}$$

where $M_{lat}$ is the modulation transfer function MTF of the subject optic nerve system, $M_{opt}$ is the modulation transfer function MTF of the optical system, $m_n$ is the contrast of the noise in the optic nerve system, $m_t$ is the contrast of the stimulus, k ($=s_0/$) is a value obtained by dividing the average $s_0$ of the contrast threshold values by the dispersion thereof, and u is a parameter representing a spatial frequency.

Second Embodiment

Figure 7:
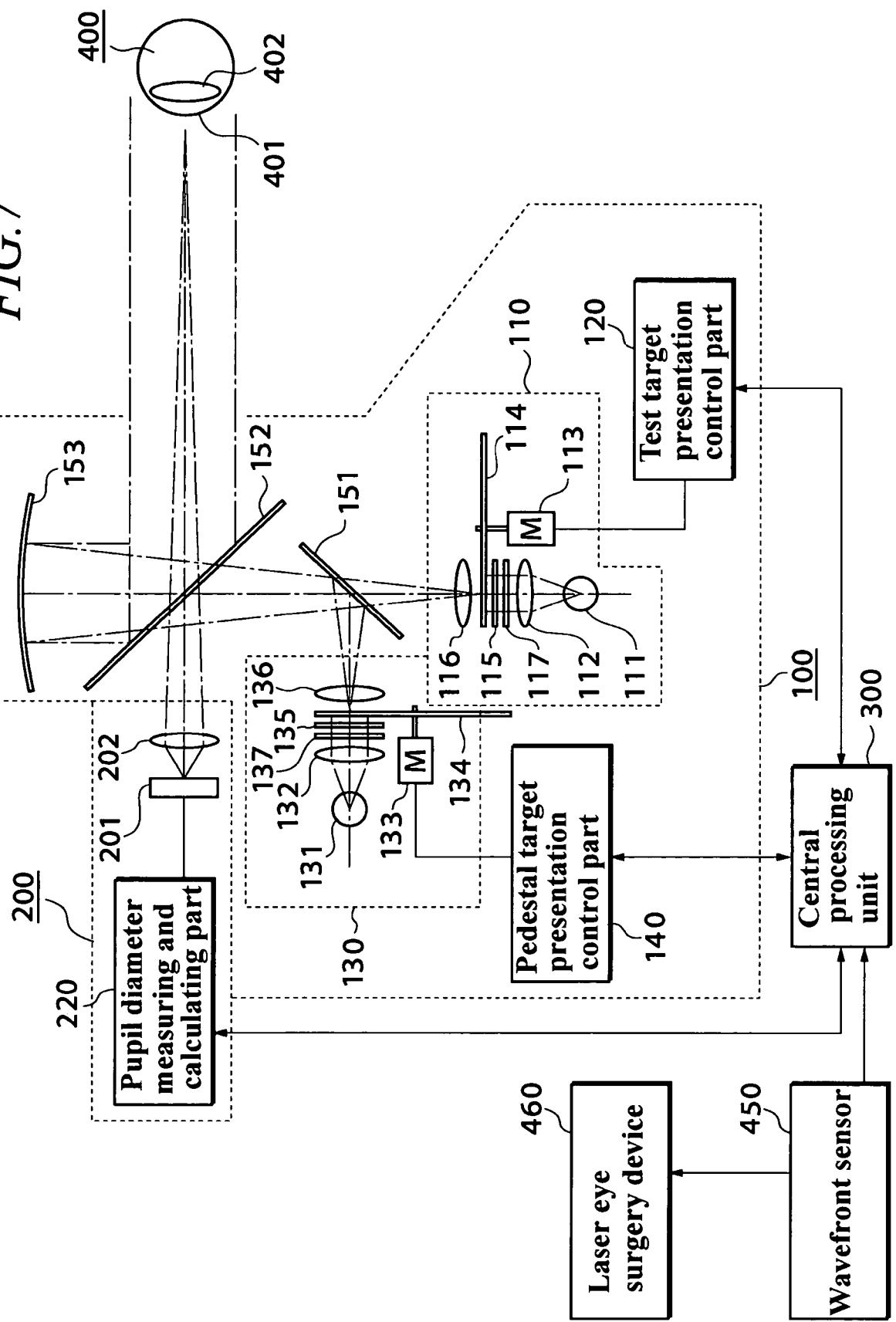
FIG. 7 is a structural view illustrating a second embodiment of the present invention.

FIG. 7 is a structural view illustrating a second embodiment of the present invention. The device shown in FIG. 7 comprises the device shown in FIG. 1, a wavefront sensor 350, and a laser eye surgery device 360. The wavefront sensor 350 measures the aberrations of a cornea or a crystalline lens constituting an eye of a subject. The main components of the wavefront sensor 350 are an array of small lenses called a small lens array and a camera having an array of sensor elements. This configuration is referred to as "Shack-Hartmann wavefront sensor" and comprises a Hartmann plate constituted of an array of small lenses which, when disposed in a path of light, produces multiple elemental portions of the light referred to as subapertured portions and photoreceptors such as CCDs located at the focal points of the small lenses. When parallel light is irradiated on the Hartmann plate, the small lens array divides the light into beams and the beams are focused onto the CCDs. When the wavefront of the incident light is distorted, the light beams are focused on points deviated from the focal points of the lenses. The wavefront can be obtained from the deviations.

The laser eye surgery device 360 is used when an ophthalmologist decides where on the surface of the eye a laser beam should be applied to change the shape of a cornea or the like and applies a laser beam to the decided spot. The central processing unit 300 is connected to the wavefront sensor 350.

In the device constituted as above, the central processing unit 300 provides a measured pupil diameter to the wavefront sensor 350. The wavefront sensor 350 measures the wavefront aberrations of the eye in advance. The wavefront sensor may be incorporated in the contrast sensitivity measuring device so that the wavefront aberrations of the eye can be measured simultaneously with the measurement of the contrast sensitivity thereof. Then, a point spread function PSF and a modulation transfer function MTF are calculated using the wavefront data measured by the wavefront sensor 350 and the measured pupil diameter. The point spread function PSF and the modulation transfer function MTF calculated in the wavefront sensor 350 are sent to the central processing unit 300. The central processing unit 300 compares the data such as the measured modulation transfer function MTF and the data such as the modulation transfer function MTF calculated in the wavefront sensor 350. As a result of the comparison, when the measured values and the calculated values indicate the same result, the optical system of the eye is assumed to have ametropia and a laser eye surgery or the like can be performed with the laser eye surgery device or the like. When the measured values and the calculated values indicate different results, there may be a pathological reason and a surgery cannot be performed.

Third Embodiment and Fourth Embodiment

Figure 8:
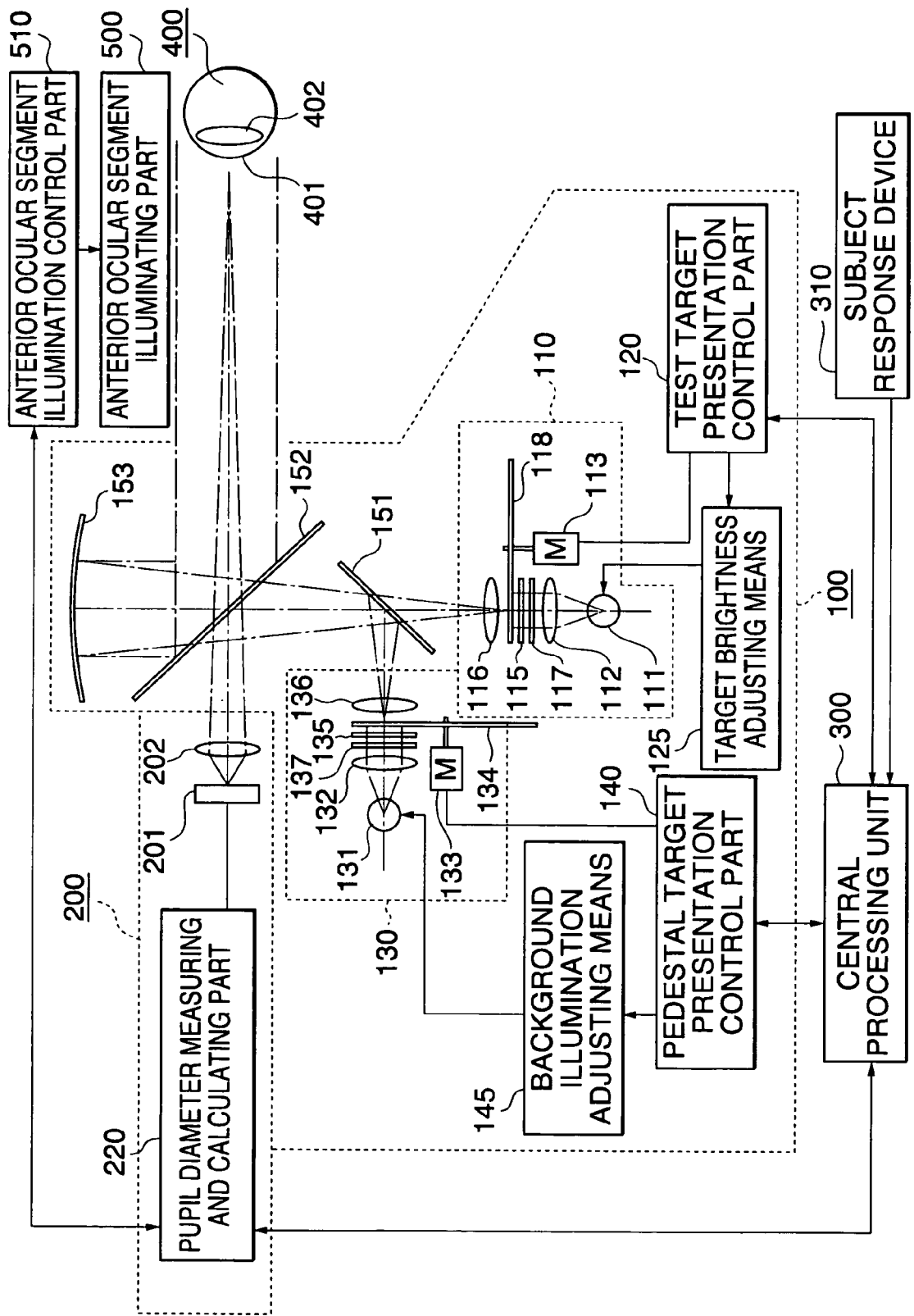
FIG. 8 is a structural view illustrating third and fourth embodiments of the present invention.

FIG. 8 is a structural view illustrating third and fourth embodiments of the present invention, in which an optical system and a control system are shown together. In FIG. 8, parts having the same functions as those in FIG. 1 are designated by the same numerals and their description will be omitted. A first illuminating optical system 110 has a target plate 118. On the target plate 118, contrast sensitivity targets suitable for measurement of modulation transfer function such as Gabor stimuli are printed as contrast targets in prescribed sizes.

A test target presentation control part 120 drives a target exchanging rotary motor 113 to move the target plate 118 to a suitable position so that an appropriate test target can be presented to a subject. The test target presentation control part 120 functions as target brightness control means for sending a brightness control signal to target brightness adjusting means 125. The test target presentation control part 120 receives the diameter of the pupil region (pupil diameter) of a subject measured by a pupil data measuring part 200 and outputs a control signal for adjusting the brightness of a contrast target so that the pupil diameter will be a prescribed value. The target brightness adjusting means 125 adjusts the electric power to adjust the light quantity of a light source 111 or changes ND filters 115 for adjusting the quantity of light transmitting therethrough in order to adjust the brightness of the contrast target.

Contrast herein is given as the difference between the transmissivities of a pedestal target and a test target. A white noise or a filtered noise stimulus with a limited bandwidth may be used as a pedestal target with a transmissivity of 100%.

A pedestal target presentation control part 140 functions as background illumination control means. The pedestal target presentation control part 140 receives the pupil diameter of the subject measured by the pupil data measuring part 200 and sends a background illumination control signal to background illumination adjusting means 145 so that the pupil diameter will be a prescribed value. The background illumination adjusting means 145 adjusts the electric power to adjust the light quantity of a light source 131 or changes ND filters 135 for adjusting the quantity of light transmitting therethrough in order to adjust the background illumination of a contrast target.

A test target (contrast target) sent from a first illuminating optical system 110 and a pedestal target (background illumination) sent from a second illuminating optical system 130 are superimposed in a light path by a mirror 151, passed through a spectral mirror 152 as a first mirror, reflected by a concave mirror 153 as a second mirror, reflected again by the spectral mirror 152 and reaches an anterior ocular segment 401 of a subject.

A subject response device 310 is used to input the responses of a subject about the contrast targets and comprises an I/O device such as a mouse. The output signals from the subject response device 310 are input into the central processing unit 300.

An anterior ocular segment illuminating part 500 illuminates the anterior ocular segment 401 and comprises a fluorescent lamp, an incandescent lamp or an LED. An anterior ocular segment illumination control part 510 receives the pupil diameter of a subject measured by the pupil data measuring part 200 and sends an illumination control signal to the anterior ocular segment illuminating part 500 so that the pupil diameter will be a prescribed value. The anterior ocular segment illumination control part 510 controls the voltage or current, for example, to be supplied to the anterior ocular segment illuminating part 500 to adjust the brightness thereof.

Figure 9:
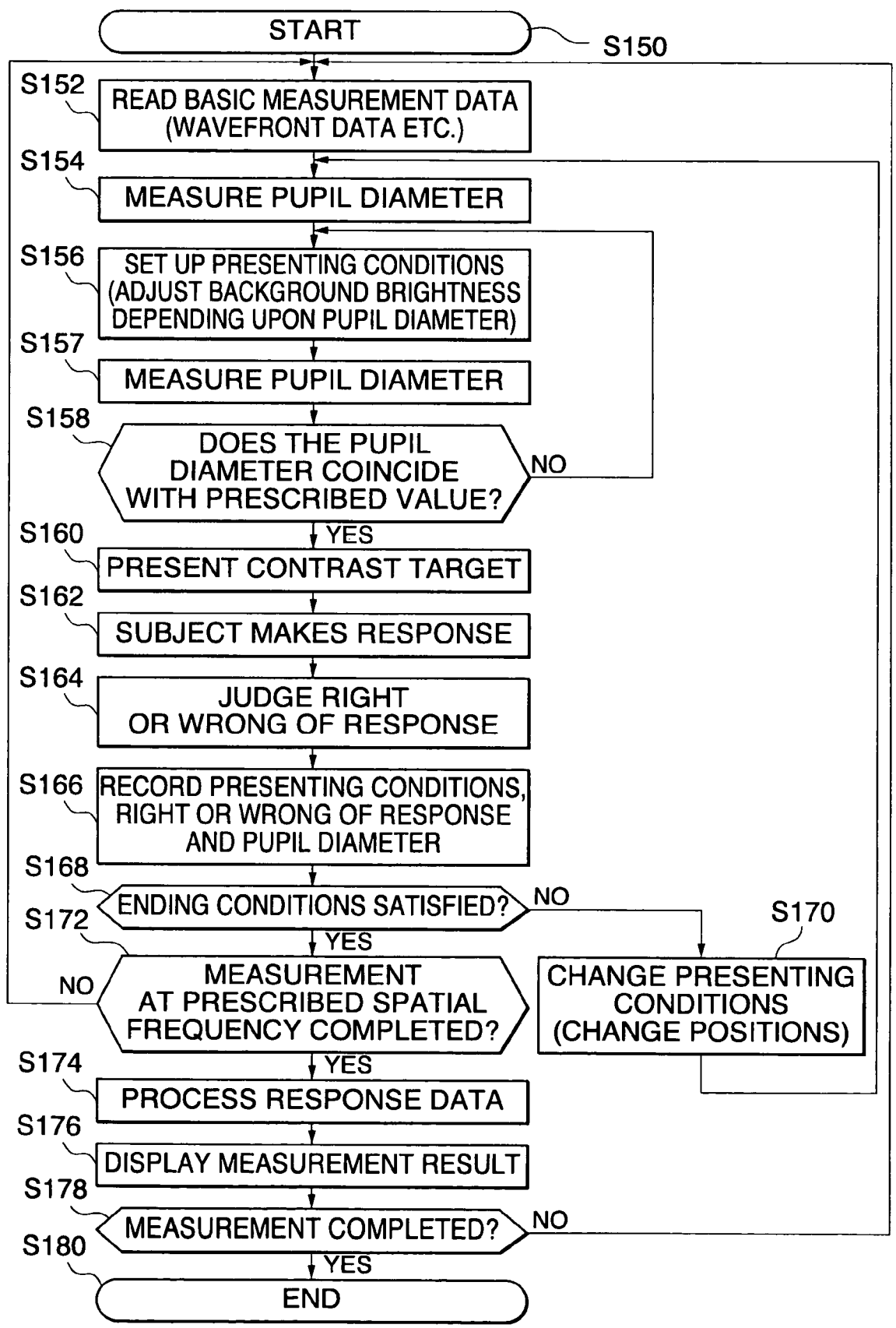
FIG. 9 is a flowchart for explaining the third embodiment of the present invention, showing a case in which the brightness of test targets is adjusted so that the pupil diameter of a subject will be a prescribed value.

FIG. 9 is a flowchart for explaining the third embodiment of the present invention, showing the case in which the brightness of the test targets is adjusted so that the pupil diameter of a subject will be a prescribed value. When measurement of contrast sensitivity is started (S150), the central processing unit 300 reads basic measurement data (S152). The basic measurement data include information on the visual acuity of the subject, data on the pupil wavefront, presence or absence of cataract, information on disorders in the optic nerve system and spatial frequencies of the targets to be presented in this measurement. Then, the pupil data measuring part 200 produces an image of the anterior ocular segment 401 of the subject and measures the diameter or the area of the pupil region (S154). The pedestal target presentation control part 140 adjusts the background brightness depending upon the pupil diameter of the subject to set up the conditions under which the test targets are presented (S156). The test target presentation control part 120 may adjust the brightness of the test target depending upon the pupil diameter of the subject to set up the conditions under which the test targets are presented. The pupil data measuring part 200 produces an image of the anterior ocular segment 401 of the subject and measures the pupil diameter (S157). Then, it is judged whether the pupil diameter of the subject coincides with the prescribed value (S158). The pupil diameter of the subject does not coincide with the prescribed value, the process returns to step S156. When the pupil diameter of the subject coincides with the prescribed value, the test target presentation control part 120 presents a contrast sensitivity target as a test target (S160).

The measurement is conducted by, for example, an up-down method, which is one of psychological measurement methods. The up-down method is a forced choice method in which a target with contrast and a target without contrast are presented side by side once in one trial and the subject responses the position where there is a Gabor stimulus. In one trial, a background is first presented to the subject and a Gabor stimulus is then presented. Then, the response of the subject is recorded. The central processing unit 300 repeatedly presents Gabor stimuli to the subject until the measurement is completed. Instead of the up-down method, a method of limits, method of adjustment, constant method, PEST, or QUEST may be employed. FIG. 10 shows examples of the manner of presenting targets. In the example shown in FIG. 10(A), a target with high contrast is on the left and a target without contrast is on the right. In the example shown in FIG. 10(B), a target with high contrast is on the right and a target without contrast is on the left.

Then, the subject makes a response about the presented contrast sensitivity targets (S162). When the up-down method, which is a two-alternative forced choice (2AFC) method, is employed for the stimulus presentation, the subject responds the position where there is a Gabor stimulus. The subject may make responses using a subject response device such as a mouse or with voice. A clinical technologist or the central processing unit 300 compares the test target presented by the test target presentation control part 120 and the response of the subject, and judges whether the response is right or wrong (S164). Then, the central processing unit 300 records the target presenting conditions, the right or wrong of the response, the pupil diameter of the subject and so forth (S166). The clinical technologist or the central processing unit 300 judges whether the number of times of presentation of a test target reaches a reference value, for example, the number of time of switches from a correct response to a wrong response and switched from a wrong response to a correct response respectively reach five as shown in FIG. 6 (S168). When the number of times of presentation has not reached the reference number, the target presenting conditions are changed (S170) and the process returns to step S154.

When the number of presentation of a test target has reaches the reference number, it is judged whether the test using contrast sensitivity targets having a prescribed spatial frequency has been completed (S172). When the test has not been completed, the process returns to step S152 and the test at the spatial frequency is continued. When the test has been completed, the response data are processed (S174) and the result is displayed (S176). Then, it is judged whether measurement using contrast targets having the other special frequencies should be performed using the history of responses of the subject and whether to finish the measurement is decided (S178). When measurement should still be performed, the process returns to step S152 and measurement using contrast targets having another special frequency or a retest is performed. When there is no need to perform measurement any more, the measurement of contrast sensitivity of the subject is completed (S180). The time for which a contrast sensitivity target is presented in one trial is 1 to 3 seconds, preferably 2 seconds from a clinical point of view.

FIG. 11 is a view illustrating an example of the history of responses of a subject about contrast sensitivity targets with various spatial frequencies, in which (A) (B) (C) and (D) show the cases in which stripe patterns of a special frequency of 3 cpd ([cycles/deg]), 6 cpd, 12 cpd and 18 cpd are used respectively. The history of the responses of the subject at each spatial frequency exhibits a similar pattern to that in the measurement of contrast sensitivity shown in FIG. 6.

Figure 12:
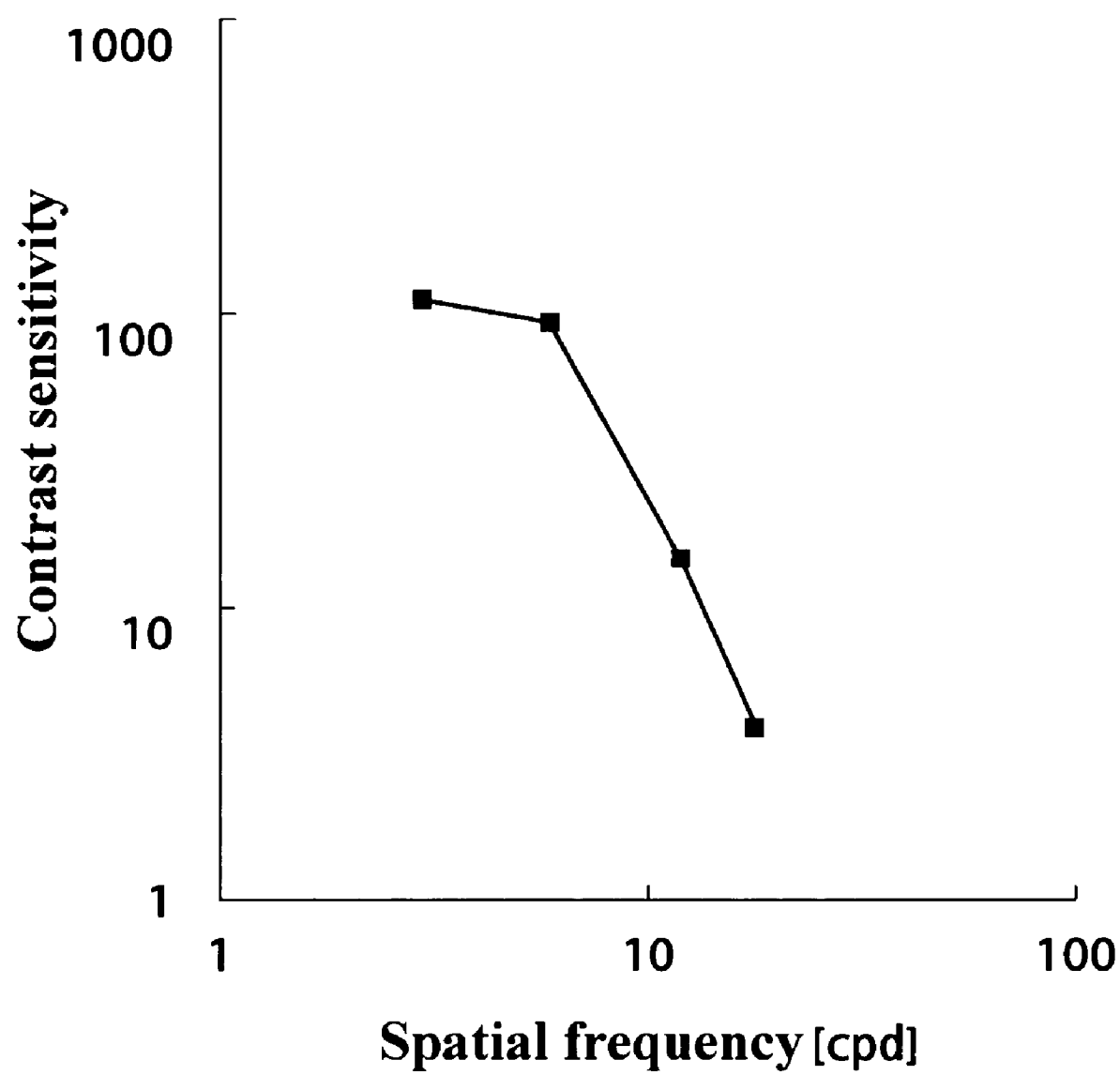
FIG. 12 is a graph showing the relation between the contrast sensitivity and the spatial frequency.

FIG. 12 is a graph showing the relation between the contrast sensitivity and the spatial frequency. Based on the history of responses of the subject at various spatial frequencies, the contrast threshold values for each spatial frequency are determined. Then, the central processing unit 300 calculates the reciprocals of the contrast threshold values to obtain the contrast sensitivities. In general, the contrast sensitivity of a subject takes the maximum value when the spatial frequency is in the range of 3 to 6 cpd and tends to decrease gradually when the spatial frequency increases to 10 cpd or higher. When a subject has an abnormal value at some spatial frequencies as compared with a standard pattern of the contrast sensitivity to the spatial frequency, there is a possibility that the subject has a pathological lesion in the pupil or optic nerves. Thus, the measurement of contrast sensitivity is suitable as an ophthalmic examination.

Figure 13:
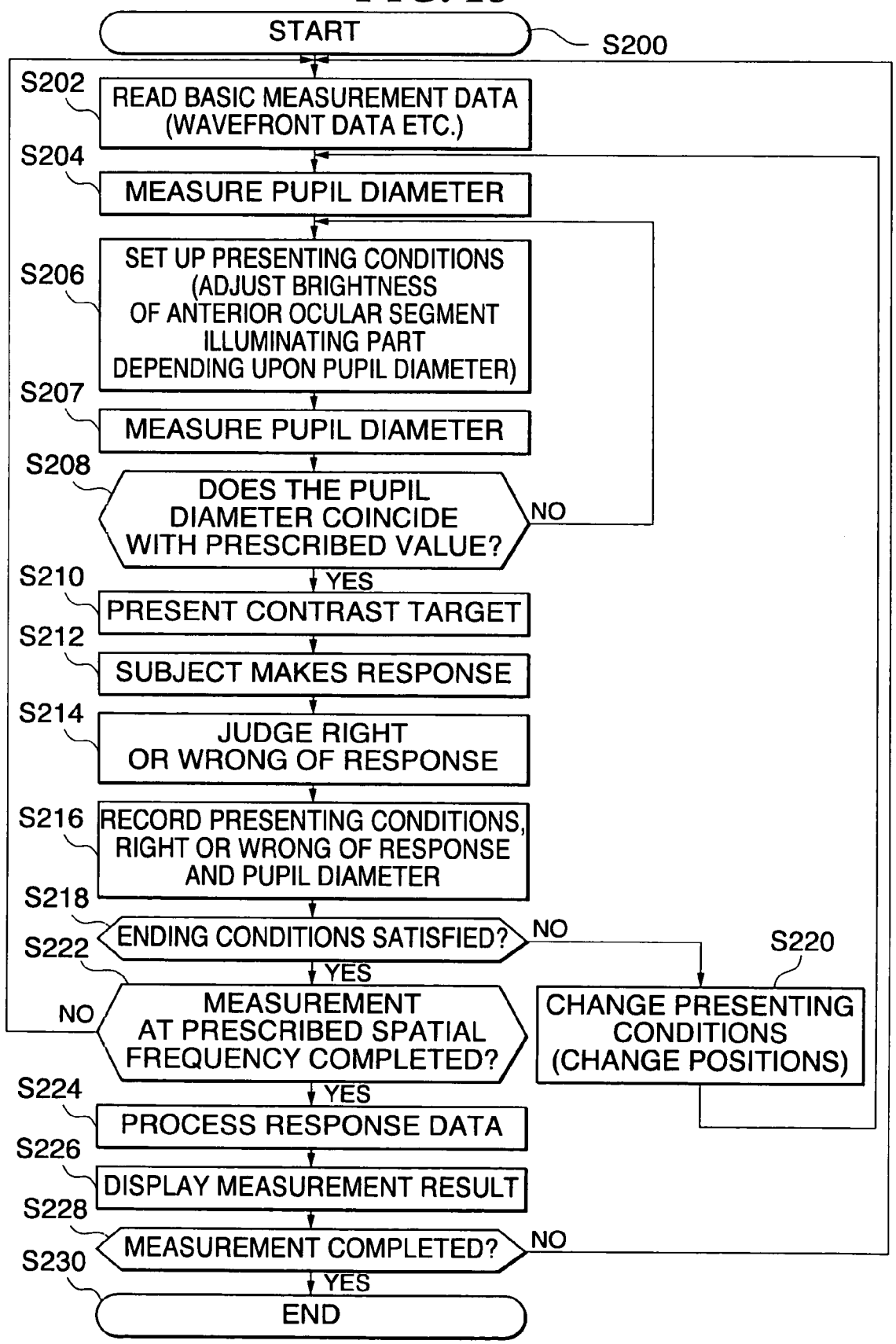
FIG. 13 is a flowchart for explaining the fourth embodiment of the present invention, showing a case in which the brightness of an anterior ocular segment illuminating part is adjusted so that the pupil diameter of the subject will be a prescribed value.

FIG. 13 is a flowchart for explaining the fourth embodiment of the present invention, showing a case in which the brightness of the anterior ocular segment illuminating part is adjusted so that the pupil diameter of the subject will be a prescribed value. Steps S200 to S204 correspond to step S150 to S154, respectively, in FIG. 9. In step S206, the anterior ocular segment illumination control means 510 sends an illumination control signal depending upon the pupil diameter of the subject and the anterior ocular segment illuminating part 500 adjusts the illuminance at the anterior ocular segment 401. Then, the pupil diameter data measuring part 200 produces an image of the anterior ocular segment 401 of the subject and measures the pupil diameter thereof (S207). Then, it is judged whether the pupil diameter of the subject coincides with the prescribed value (S208). When the pupil diameter of the subject does not coincide with the prescribed value, the process returns to step S206. When the pupil diameter of the subject coincides with the prescribed value, the test target presentation control part 120 presents a contrast sensitivity target as a test target (S210). Steps S210 to S230 correspond to step S160 to S180, respectively, in FIG. 9.

Fifth Embodiment and Sixth Embodiment

Figure 14:
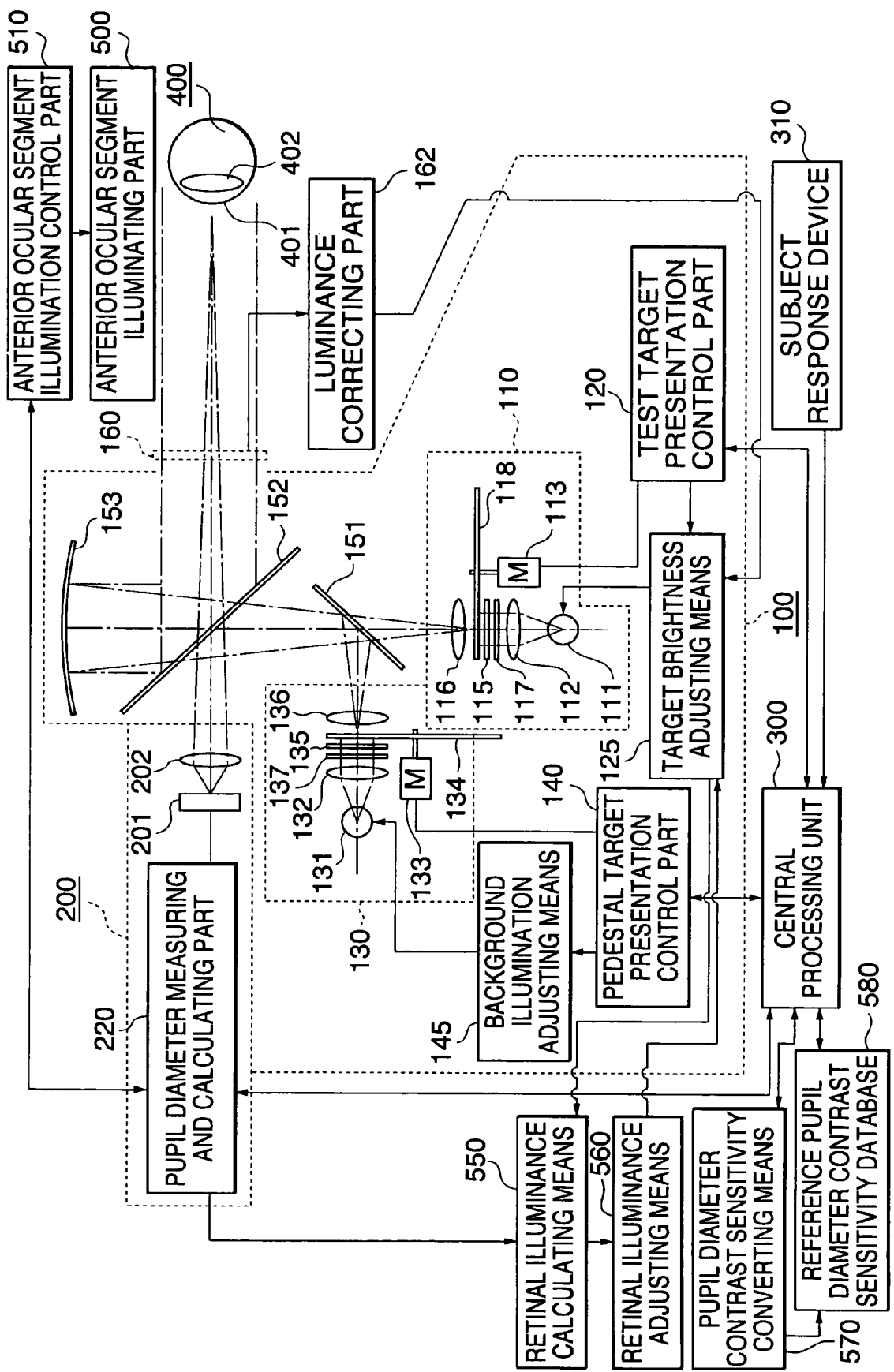
FIG. 14 is a structural view illustrating fifth and sixth embodiments of the present invention.

FIG. 14 is a structural view illustrating fifth and sixth embodiments of the present invention, in which an optical system and a control system are shown together. In FIG. 14, parts having the same functions as those in FIG. 8 are designated by the same numerals and their description will be omitted. A luminance measuring part 160 in FIG. 14 measures the luminance of a target presented in the contrast target presenting part 100 and comprises an illuminance meter or a power meter without luminous efficacy filter. The unit of the values measured by an illuminance meter is cd (candela) and the luminance of the presented target is expressed in [cd/m$^2$]. The illuminance meter is located in a light path between a light detection camera lens system 202 and the anterior ocular segment 401.

When a CRT monitor or a liquid crystal display is used as the device for presenting the contrast targets, the illuminance and the luminance thereof vary almost in proportion to each other. Thus, by measuring the illuminance of the CRT monitor, the luminance thereof can be substantially measured. A luminance correcting part 162 corrects the luminance of the contrast target based on the luminance thereof measured by the luminance measuring part 160. By the correction with the luminance correcting part 162, the effect of secular changes in the contrast target presenting part 100 can be eliminated.

Retinal illuminance calculating means 550 calculates the retinal illuminance of an eye to be examined from the diameter, preferably the area, of the pupil region measured by the pupil data measuring part 200 and the brightness, luminance, in particular, of a contrast target presented by the test target presentation control part 120. The retinal illuminance T is obtained from the following equation;

$$T = A/L \quad (2)$$

where A represent the area [mm$^2$] of the pupil region and L represents the luminance [cd/m$^2$] of the target. The unit of the illuminance T is Troland (td).

Retinal illuminance adjusting means 560 outputs a control signal so that the retinal illuminance of the eye to be examined will be generally constant. For example, the retinal illuminance adjusting means 560 outputs a signal for adjusting the brightness of a contrast target to target brightness adjusting means 125, outputs a signal for adjusting the brightness of the background illumination of the contrast target to the background illumination adjusting means 145, or outputs a signal for adjusting the brightness of anterior ocular segment illuminating part 500 to anterior illumination control part 510. This is to make the retinal illuminance of the eye to be examined constant since the contrast sensitivity of an eye varies depending upon the retinal illuminance thereof (for example, the contrast sensitivity in the day is different from that at night).

Pupil diameter contrast sensitivity converting means 570 reads the pupil diameter of the subject at the time when the contrast sensitivity was measured from the pupil data measuring part 200, converts the measured contrast sensitivity into a contrast sensitivity which would be obtained when the pupil diameter is a reference value, and stores the result in a reference pupil diameter contrast sensitivity database 580. Although the retinal illuminance adjusting means adjusts the retinal illuminance of the eye to be examined so that the pupil diameter thereof will be constant, it takes several dozen seconds to a few minutes for the pupil to react to the change in brightness. Thus, in order to perform measurement of contrast sensitivity quickly and enhance the measurement accuracy, the pupil diameter contrast sensitivity converting means 570 compensates for the part of the contrast sensitivity which varies depending upon the pupil diameter. In the reference pupil diameter contrast sensitivity database 580, the contrast sensitivity, the part of which varies depending upon the pupil diameter has been compensated for, is stored.

Figure 15:
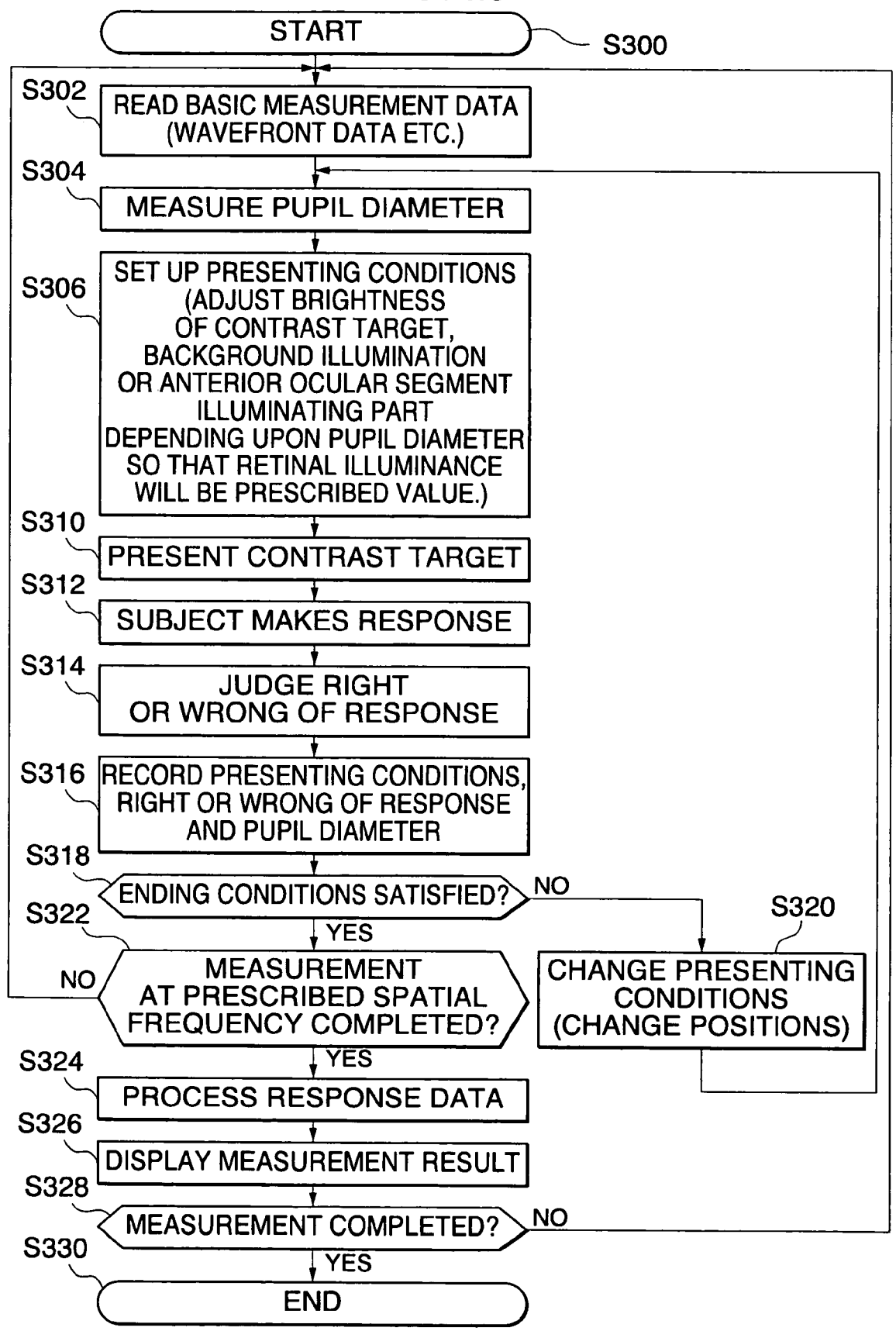
FIG. 15 is a flowchart for explaining the fifth embodiment of the present invention, showing a case in which the brightness is adjusted so that the retinal illuminance of the subject will be a prescribed value.

FIG. 15 is a flowchart for explaining the fifth embodiment of the present invention, showing a case in which the brightness is adjusted so that the retinal illuminance of the subject will be a prescribed value. Steps S300 to S304 correspond to step S150 to S154, respectively, in FIG. 9. In step S306, the retinal illuminance calculating means 550 calculates the retinal illuminance of the subject. Then, the retinal illuminance adjusting means 560 outputs a control signal to the target brightness adjusting means 125, the background illumination adjusting means 145, or the anterior ocular segment illumination control means 510 so that the retinal illuminance of the eye to be examined will be generally constant. Steps S310 to S330 correspond to step S160 to S180, respectively, in FIG. 9.

Figure 16:
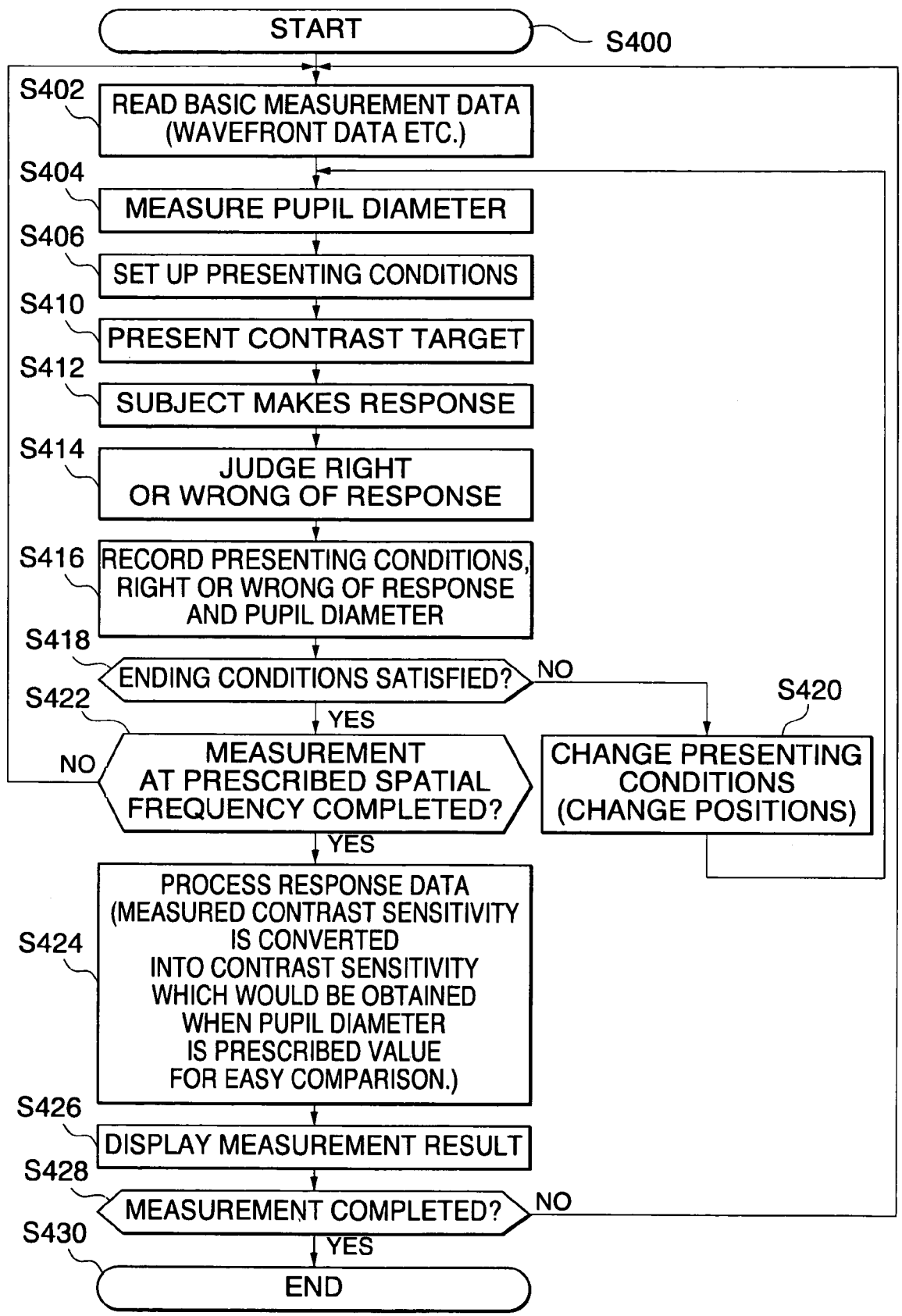
FIG. 16 is a flowchart for explaining the sixth embodiment of the present invention, showing a case in which the contrast sensitivity and the pupil diameter of the subject is measured at a constant contrast target brightness and the measured contrast sensitivity is converted into a contrast sensitivity which would be obtained when the pupil diameter is a prescribed value.

FIG. 16 is a flowchart for explaining the sixth embodiment of the present invention, showing a case in which the contrast sensitivity and the pupil diameter of the subject is measured at a constant contrast target brightness and the measured contrast sensitivity is converted into a contrast sensitivity which would be obtained when the pupil diameter is a prescribed value. Steps S400 to S404 correspond to step S150 to S154, respectively, in FIG. 9. In step S406, the brightness of the background or a test target is adjusted depending upon the pupil diameter of the subject. Steps S410 to S422 correspond to step S160 to S172, respectively, in FIG. 9.

In the processing of response data in step S424, the pupil diameter contrast sensitivity converting means 570 reads the pupil diameter at the time when the contrast sensitivity was measured from the pupil data measuring part 200 and converts the measured contrast sensitivity into a contrast sensitivity which would be obtained when the pupil diameter is a reference value. The result is stored in, for example, a reference pupil diameter contrast sensitivity database 580. Since the contrast sensitivity of an eye varies depending upon the pupil diameter thereof, the pupil diameter is preferably kept constant. However, it takes several dozen seconds to a few minutes for the pupil to react to the change in brightness. Thus, the processing of response data in step S424 may be performed in order to perform the measurement of contrast sensitivity quickly and enhance the measurement accuracy. Steps S426 to S430 correspond to step S176 to S180, respectively, in FIG. 9.

In the above embodiments, an example in which the test targets are sent from the first illuminating optical system 110 and the pedestal targets are sent from the second illuminating optical system 130 has been described. However, the target plates 118 and 134 may be interchanged so that the pedestal targets are sent from the first illuminating optical system 110 and the test targets are sent from the second illuminating optical system 130. Also, in the above embodiments, the contrast produced by a pedestal target and a test target is varied using the target plate 118. However, the contrast may be varied by changing the light quantity of the light source 131 and 111 or the transmissivity (density) of the ND filter 135 and 115.

In the above embodiments, the measurement of contrast sensitivity is performed on one eye of a subject at a time.

However, the contrast sensitivities of both eyes may be measured simultaneously. In this case, when the subject wears polarized glasses, a full-fledged stereoscopic test can be performed. In the above embodiments, an example in which the test target presentation control part 120 having a function as target brightness control means, the target brightness adjusting means 125, the pedestal target presentation control part 140 having a function as background illumination control means and the background illumination adjusting means 145 are provided in the contrast target presenting part 100. However, those components may be provided in the central processing unit 300 as long as they function integrally with the first illuminating optical system 110 and the second illuminating optical system 130.

INDUSTRIAL APPLICABILITY

The contrast chart device of the present invention comprises: a contrast target presenting part for presenting a contrast target for a contrast sensitivity test at prescribed timing; a pupil data measuring part for producing an image of an anterior ocular segment of a subject and measuring the diameter or area of a pupil region in the anterior ocular segment; and a measurement timing forming part for forming timing at which the pupil data measuring part performs measurement based on the prescribed timing. Thus, the contrast sensitivity and the pupil diameter of the subject can be simultaneously measured. Therefore, when the diameter or area of the pupil region of a subject varies, the effect of the change can be grasped and the contrast sensitivity can be measured precisely.

The contrast sensitivity measuring device of the present invention comprises a contrast target presenting part for presenting first and second contrast targets side by side; a pupil data measuring part for producing an image of an anterior ocular segment of a subject and measuring the diameter or area of a pupil region in the anterior ocular segment; and a measurement timing forming part for forming timing at which the pupil data measuring part performs measurement based on the timing at which the contrast target presenting part presents the first and second contrast targets. Thus, the contrast sensitivity of a subject can be measured precisely within a short period of time.

In the contrast sensitivity measuring device of the present invention, the presentation of stimuli and the reception of responses of a subject are performed by the contrast target presenting part and the measurement timing forming part, respectively. Thus, since the clinical technologist or ophthalmologist needs only to check whether an unusual event is occurring to the subject, the examination time can be shortened.

Also in an embodiment of the present invention, the contrast target presenting part is configured to change the target presenting position at random in each trial. This makes the memory of the subject on the positions of the contrast targets in a previous trial useless, and the subject makes a response based only on the information obtained from a stimulus which it can see in each trial. Thus, the contrast sensitivity of the subject can be measured precisely.

Also in the contrast sensitivity measuring device of the present invention, since the pupil data measuring part measures the pupil diameter of a subject, a control signal can be output to the target brightness adjusting means, the background illumination adjusting means or the anterior ocular segment illumination control means so that the pupil diameter or the retinal illuminance of the subject will be generally constant. Thus, a visual function test can be easily performed even in a dark place.

What is claimed is:

1. A contrast chart device, comprising:
    a contrast target presenting part for presenting a contrast target changing a contrast for a contrast sensitivity test at prescribed timing;
    a pupil data measuring part for producing an image of an anterior ocular segment of a subject and measuring the diameter or area of a pupil region in said anterior ocular segment; and
    a measurement timing forming part for forming timing at which said pupil data measuring part performs measurement based on said prescribed timing,
    wherein said contrast target presenting part has:
    background illumination adjusting means for adjusting illuminance of a background illumination of said contrast target or contrast targets in order to maintain the retinal illuminance of said subject at generally prescribed value; and
    background illumination control means which receives the diameter or area of said pupil region of said subject measured by said pupil data measuring part and sends a background illumination control signal to said background illumination adjusting means so that the diameter or area of said pupil region will be a prescribed value.

2. A contrast chart device as claimed in claim 1,
    wherein said contrast target presenting part has a first illuminating optical system for mainly forming targets and a second illuminating optical system for mainly forming backgrounds, and is so constituted that luminous fluxes from said first illuminating optical system and said second illuminating optical system are combined, passed through a first mirror for folding a light path, reflected by a second mirror, and reflected again by said first mirror to an eye to be examined.

3. A contrast chart device as claimed in claim 2,
    wherein said first illuminating optical system is so constituted that targets of various sizes can be selectively inserted into a light path therein.

4. A contrast chart device as claimed in claim 2,
    wherein said second illuminating optical system is configured to be able to produce a luminous flux with uniform light distribution in different brightnesses.

5. A contrast chart device as claimed in claim 2,
    wherein said pupil data measuring part is configured to produce said image of an anterior ocular segment of said subject and measure the diameter or area of a pupil region in said anterior ocular segment through said first mirror.

6. A contrast chart device as claimed in claim 1,
    wherein said pupil data measuring part is configured to measure the diameter or area of said pupil region of said subject when said contrast target is presented or said subject makes a response.

7. A contrast chart device as claimed in claim 1,
    configured to be able to output to a device for measuring the wavefront aberrations of the eye at least said measured diameter or area of said pupil region of said subject and a contrast target presented when the pupil data are measured.

8. A contrast sensitivity measuring device, comprising:
    a contrast target presenting part for presenting a contrast target changing a contrast for a contrast sensitivity test at prescribed timing;

a pupil data measuring part for producing an image of an anterior ocular segment of a subject and measuring the diameter or area of a pupil region in said anterior ocular segment; and a measurement timing forming part for forming timing at which said pupil data measuring part performs measurement based on said prescribed timing, wherein said contrast target presenting part has:

background illumination adjusting means for adjusting illuminance of a background illumination of said contrast target or contrast targets in order to maintain the retinal illuminance of said subject at a generally prescribed value; and background illumination control means which receives the diameter or area of said pupil region of said subject measured by said pupil data measuring part and sends a background illumination control signal to said background illumination adjusting means so that the diameter or area of said pupil region will be a prescribed value.

9. A contrast sensitivity measuring device as claimed in claim 8, wherein said contrast target presenting part has:

target brightness adjusting means for adjusting the brightness of said contrast target or contrast targets; and target brightness control means which receives the diameter or area of said pupil region of said subject measured by said pupil data measuring part and sends a brightness control signal to said target brightness adjusting means so that the diameter or area of said pupil region will be a prescribed value.

10. A contrast sensitivity measuring device as claimed in claim 8, wherein said pupil data measuring part is configured to produce an image of said anterior ocular segment of said subject and measure the diameter or area of said pupil region of said subject before and when the measurement of contrast sensitivity is performed.

11. A contrast sensitivity measuring device as claimed in claim 8, wherein said pupil data measuring part is configured to measure the diameter or area of said pupil region of said subject when said contrast target or contrast targets is or are presented or said subject makes a response.

12. A contrast sensitivity measuring device as claimed in claim 8, further comprising:

an anterior ocular segment illuminating part for illuminating an anterior ocular segment; and anterior ocular segment illumination control means which receives the diameter or area of said pupil region of said subject measured by said pupil data measuring part and sends an illumination control signal to said anterior ocular segment illuminating part so that the diameter or area of said pupil region will be a prescribed value.

13. A contrast sensitivity measuring device as claimed in claim 8, further comprising:

a luminance measuring part for measuring the luminance of said contrast target or contrast targets presented by said contrast target presenting part; and a luminance correcting part for correcting said luminance of said contrast target or contrast targets based on the luminance measured by said luminance measuring part.

14. A contrast sensitivity measuring device as claimed in claim 8, further comprising:

retinal illuminance calculating means for calculating the retinal illuminance of an eye to be examined from the diameter or area of said pupil region of said eye to be examined and the brightness of said contrast target or contrast targets; and retinal illuminance adjusting means for outputting a signal for adjusting the brightness of said contrast target or contrast targets to said target brightness adjusting means so that the retinal illuminance of said eye to be examined will be generally constant, and configured to measure the contrast sensitivity of said eye to be examined with said retinal illuminance of said eye to be examined maintained generally constant.

15. A contrast sensitivity measuring device as claimed in claim 8, further comprising:

pupil diameter contrast sensitivity converting means which reads the diameter or area of said pupil region of said subject at the time of measurement of contrast sensitivity from said pupil data measuring part and converts a measured contrast sensitivity into a contrast sensitivity which would be obtained when said pupil diameter is a reference value.

16. A contrast sensitivity measuring device as claimed in claim 8, wherein said contrast target or contrast targets is or are a contrast sensitivity target or contrast sensitivity targets.

17. A contrast sensitivity measuring device, comprising:

a contrast target presenting part for presenting first and second targets side by side changing a contrast for a contrast sensitivity test at a prescribed timing;

a pupil data measuring part for producing an image of an anterior ocular segment of a subject and measuring the diameter or area of a pupil region in said anterior ocular segment; and a measurement timing forming part for forming timing at which said pupil data measuring part performs measurement based on the timing at which said contrast target presenting part presents said first and second contrast targets, wherein said contrast target presenting part has: background illumination adjusting means for adjusting illuminance of a background illumination of said contrast target or contrast targets in order to maintain the retinal illuminanee of said subject at a generally prescribed value; and background illumination control means which receives the diameter or area of said pupil region of said subject measured by said pupil data measuring part and sends a background illumination control signal to said background illumination adjusting means so that the diameter or area of said pupil region will be a prescribed value.

18. A contrast sensitivity measuring device as claimed in claim 17, wherein one of said first and second contrast targets is a target with a contrast of 0 and the other is a target with a contrast for measuring contrast sensitivity.

19. A contrast sensitivity measuring device as claimed in claim 17, wherein said contrast target presenting part has:

target brightness adjusting means for adjusting the brightness of said contrast target or contrast targets; and target brightness control means which receives the diameter or area of said pupil region of said subject measured by said pupil data measuring part and sends a brightness control signal to said target brightness adjusting means so that the diameter or area of said pupil region will be a prescribed value.

20. A contrast sensitivity measuring device as claimed in claim 17,
wherein said pupil data measuring part is configured to produce an image of said anterior ocular segment of said subject and measure the diameter or area of said pupil region of said subject before and when the measurement of contrast sensitivity is performed.

21. A contrast sensitivity measuring device as claimed in claim 17,
wherein said pupil data measuring part is configured to measure the diameter or area of said pupil region of said subject when said contrast target or contrast targets is or are presented or said subject makes a response.

22. A contrast sensitivity measuring device as claimed in claim 17, further comprising:
an anterior ocular segment illuminating part for illuminating an anterior ocular segment; and
anterior ocular segment illumination control means which receives the diameter or area of said pupil region of said subject measured by said pupil data measuring part and sends an illumination control signal to said anterior ocular segment illuminating part so that the diameter or area of said pupil region will be a prescribed value.

23. A contrast sensitivity measuring device as claimed in claim 17, further comprising:
a luminance measuring part for measuring the luminance of said contrast target or contrast targets presented by said contrast target presenting part; and
a luminance correcting part for correcting said luminance of said contrast target or contrast targets based on the luminance measured by said luminance measuring part.

24. A contrast sensitivity measuring device as claimed in claim 17, further comprising:
retinal illuminance calculating means for calculating the retinal illuminance of an eye to be examined from the diameter or area of said pupil region of said eye to be examined and the brightness of said contrast target or contrast targets; and
retinal illuminance adjusting means for outputting a signal for adjusting the brightness of said contrast target or contrast targets to said target brightness adjusting means so that the retinal illuminance of said eye to be examined will be generally constant, and
configured to measure the contrast sensitivity of said eye to be examined with said retinal illuminance of said eye to be examined maintained generally constant.

25. A contrast sensitivity measuring device as claimed in claim 17, further comprising:
pupil diameter contrast sensitivity converting means which reads the diameter or area of said pupil region of said subject at the time of measurement of contrast sensitivity from said pupil data measuring part and converts a measured contrast sensitivity into a contrast sensitivity which would be obtained when said pupil diameter is a reference value.

26. A contrast sensitivity measuring device as claimed in claim 17,
wherein said contrast target or contrast targets is or are a contrast sensitivity target or contrast sensitivity targets.

27. A contrast sensitivity measuring device, comprising:
a contrast target presenting part for presenting a contrast target in at least one of two positions at random changing a contrast for a contrast sensitivity test at a prescribed timing;
a pupil data measuring part for producing an image of an anterior ocular segment of a subject and measuring the diameter or area of a pupil region in said anterior ocular segment; and
a measurement timing forming part for forming timing at which said pupil data measuring part performs measurement based on the timing at which said contrast target presenting part presents said contrast target,
wherein said contrast target presenting part has:
background illumination adjusting means for adjusting illuminance of a background illumination of said contrast target or contrast targets in order to maintain the retinal illuminance of said subject at a generally prescribed value; and
background illumination control means which receives the diameter or area of said pupil region of said subject measured by said pupil data measuring part and sends a background illumination control signal to said background illumination adjusting means so that the diameter or area of said pupil region will be a prescribed value.

28. A contrast sensitivity measuring device as claimed in claim 27,
wherein said contrast target presenting part has:
target brightness adjusting means for adjusting the brightness of said contrast target or contrast targets; and
target brightness control means which receives the diameter or area of said pupil region of said subject measured by said pupil data measuring part and sends a brightness control signal to said target brightness adjusting means so that the diameter or area of said pupil region will be a prescribed value.

29. A contrast sensitivity measuring device as claimed in claim 27,
wherein said pupil data measuring part is configured to produce an image of said anterior ocular segment of said subject and measure the diameter or area of said pupil region of said subject before and when the measurement of contrast sensitivity is performed.

30. A contrast sensitivity measuring device as claimed in claim 27,
wherein said pupil data measuring part is configured to measure the diameter or area of said pupil region of said subject when said contrast target or contrast targets is or are presented or said subject makes a response.

31. A contrast sensitivity measuring device as claimed in claim 27, further comprising:
an anterior ocular segment illuminating part for illuminating an anterior ocular segment; and
anterior ocular segment illumination control means which receives the diameter or area of said pupil region of said subject measured by said pupil data measuring part and sends an illumination control signal to said anterior ocular segment illuminating part so that the diameter or area of said pupil region will be a prescribed value.

32. A contrast sensitivity measuring device as claimed in claim 27, further comprising:
a luminance measuring part for measuring the luminance of said contrast target or contrast targets presented by said contrast target presenting part; and
a luminance correcting part for correcting said luminance of said contrast target or contrast targets based on the luminance measured by said luminance measuring part.

33. A contrast sensitivity measuring device as claimed in claim 27, further comprising:
retinal iliuminance calculating means for calculating the retinal illuminance of an eye to be examined from the diameter or area of said pupil region of said eye to be examined and the brightness of said contrast target or contrast targets; and retinal illuminance adjusting means for outputting a signal for adjusting the brightness of said contrast target or contrast targets to said target brightness adjusting means so that the retinal iliuminance of said eye to be examined will be generally constant, and configured to measure the contrast sensitivity of said eye to be examined with said retinal illuminance of said eye to be examined maintained generally constant.

34. A contrast sensitivity measuring device as claimed in claim 27, further comprising:

pupil diameter contrast sensitivity converting means which reads the diameter or area of said pupil region of said subject at the time of measurement of contrast sensitivity from said pupil data measuring part and converts a measured contrast sensitivity into a contrast sensitivity which would be obtained when said pupil diameter is a reference value.

35. A contrast sensitivity measuring device as claimed in claim 27, wherein said contrast target or contrast targets is or are a contrast sensitivity target or contrast sensitivity targets.

* * * * *